(12) United States Patent
Karbassi et al.

(10) Patent No.: US 8,173,103 B2
(45) Date of Patent: May 8, 2012

(54) INHIBITION OF CANCER METASTASIS

(75) Inventors: Behjatolah M. Karbassi, Little Rock, AR (US); Thomas Kieber-Emmons, Little Rock, AR (US)

(73) Assignee: The Board of Trustees of the University of Arkansa, Little Rock, AR (US)

( * ) Notice: Subject to any disclaimer, the term of this patent is extended or adjusted under 35 U.S.C. 154(b) by 650 days.

(21) Appl. No.: 12/286,950

(22) Filed: Oct. 4, 2008

(65) Prior Publication Data

US 2009/0136488 A1 May 28, 2009

Related U.S. Application Data

(63) Continuation-in-part of application No. 11/694,370, filed on Mar. 30, 2007.

(60) Provisional application No. 60/788,018, filed on Mar. 31, 2006.

(51) Int. Cl.
*C12N 9/10* (2006.01)
*C12Q 1/48* (2006.01)
*A61K 49/00* (2006.01)

(52) U.S. Cl. .............................. 424/9.2; 435/4; 435/193

(58) Field of Classification Search ............... 435/193.1, 435/4; 424/9.2
See application file for complete search history.

(56) References Cited

U.S. PATENT DOCUMENTS

2006/0154370 A1  7/2006 Chen
2007/0231332 A1  10/2007 Karbassi

OTHER PUBLICATIONS

Ito, Y., et al., The Journal of Biological Chemistry, 275(44): 34728-34736, 2000.*
Maccarana, M. et al., Journal of Biological Chemistry, 281(17): 11560-11568, 2006.*
Kalathas, D., et al., Head & Neck Oncology, 2:27, 1-8, 2010.*
Schmidt, H. H., et al., Oncogene 23: 6991-6996, 2004.*
Uyama T, Kitagawa H, Tamura Ji J, Sugahara K. Molecular cloning and expression of human chondroitin N-acetylgalactosaminyltransferase: the key enzyme for chain initiation and elongation of chondroitin/dermatan sulfate on the protein linkage region tetrasaccharide shared by heparin/heparan sulfate. J Biol Chem. Mar. 15, 2002;277(11):8841-6.).
Uyama, T. et al., 2006. Chondroitin 4-O-sulfotransferase-1 regulates E disaccharide expression of chondroitin sulfate required for herpes simplex virus infectivity J. Biol. Chem. 281:38668-38674.
Li, J-P et al., 2001, Characterization of the D-glucuronyl C5-epimerase involved in the biosynthesis of heparin and heparan sulfate. J. Biol. Chem. 276:20069-20077.
Campbell, P. et al., 1994, Biosynthesis of heparin/heparan sulfate. Purification of the D-glucuronyl C-5 epimerase from bovine liver J. Biol. Chem. 269:26953-26958.
Erfurt C, Sun Z, Haendle I et al. 2007. Tumor-reactive CD4+ T cell responses to the melanoma-associated chondroitin sulphate proteoglycan in melanoma patients and healthy individuals in the absence of autoimmunity. J. Immunology 178:7703-7709.
Li, J.P. et al., 1997, Biosynthesis of heparin/heparan sulfate. cDNA cloning and expression of D-glucuronyl C5-epimerase from bovine lung. J. Biol. Chem. 272:28158-28163.
Ito, Y. et al., 2000, Purification and characterization of N-acetylgalactosamine 4-sulfate 6-O-sulfotransferase from the squid cartilage. J. Biol. Chem. 275:34728-34736.
2008 Genbank NM_001897.4.
2008 Genbank NM_001006946.1.
2008 Genbank NM_002999.2.
2008 Genbank NM_003873.5.
Patra SK, et al. 2002. DNA methyltransferase and demethylase in human prostate cancer, Mol Carcinog. 33(3):163-71.
Leakey Ti et al. 2008. A simple algorithm for quantifying DNA methylation levels on multiple independent CpG sites in bisulfite genomic sequencing electropherograms. Nucleic Acids Res. 36(11):e64.
Thomassin H, Kress C, Grange T. 2004. MethylQuant: a sensitive method for quantifying methylation of specific cytosines within the genome. Nucleic Acids Res. 32(21):e168.
2008, GenBank Accession No. NP_000149.
1995, Genbank U27328.1.
Fukushi, Y., Nudelman, E., Levery, S. B., Hakomori, S., and Rauvala, H. 1984. Novel fucolipids accumulating in human adenocarcinoma. III. A hybridoma antibody (FH6) defining a human cancer-associated difucoganglioside (VI3NeuAcV3III3Fuc2nLc6). J Biol Chem, 259: 10511-10517.
Fukushima, K., Hirota, M.,et al. 1984. Characterization of sialosylated Lewisx as a new tumor-associated antigen. Cancer Res, 44: 5279-5285.
Hanai, N., Shitara, K., and Yoshida, H. 1986. Generation of monoclonal antibodies against human lung squamous cell carcinoma and adenocarcinoma using mice rendered tolerant to normal human lung. Cancer Res, 46: 4438-4443.
Hoff, S. D., Matsushita, Y., Ota, D. M., Cleary, K. R., Yamori, T., Hakomori, S., and Irimura, T. 1989. Increased expression of sialyl-dimeric LeX antigen in liver metastases of human colorectal carcinoma. Cancer Res, 49: 6883-6888.
Dohi, T., Nemoto, T., Ohta, S., Shitara, K., Hanai, N., Nudelman, E., Hakomori, S., and Oshima, M. 1993. Different binding properties of three monoclonal antibodies to sialyl Le(x) glycolipids in a gastric cancer cell line and normal stomach tissue. Anticancer Res, 13: 1277-1282. Koenig, A., Norgard-Sumnicht, K., Linhardt, R., and Varki, A. 1998. Differential interactions of heparin and heparan sulfate glycosaminoglycans with the selecting. Implications for the use of unfractionated and low molecular weight heparins as therapeutic agents. J Clin Invest, 101: 877-889.
Kawashima, H., Atarashi, K., Hirose, M., Hirose, J., Yamada, S., Sugahara, K., and Miyasaka, M. 2002. Oversulfated chondroitin/dermatan sulfates containing GlcAbeta1/IdoAalpha1-3GalNAc(4,6-O-disulfate) interact with L- and P-Selectin and chemokines. J Biol Chem, 277: 12921-12930.
Stevenson, J. L., Choi, S. H., and Varki, A. 2005. Differential metastasis inhibition by clinically relevant levels of heparins—correlation with selectin inhibition, not antithrombotic activity. Clin Cancer Res, 11: 7003-7011.
Monzavi-Karbassi, B., Artaud, C., Jousheghany, F., Hennings, L., Carcel-Trullols, J., Shaaf, S., Korourian, S., and Kieber-Emmons, T. 2005. Reduction of Spontaneous Metastases through Induction of Carbohydrate Cross-Reactive Apoptotic Antibodies. J Immunol, 174: 7057-7065.

(Continued)

Primary Examiner — Alana Harris Dent
Assistant Examiner — Anne Holleran
(74) Attorney, Agent, or Firm — Hugh McTavish

(57) ABSTRACT

P-Selectin on platelets and endothelium binds cell surface chondroitin sulfate (CS) proteoglycans, which are abundantly and stably expressed on the surface many cancer cells. Binding of the cancer cells through the CS moieties may be blocked to inhibit the interaction of cancer cells with platelets and endothelium. The present inventors disclose compositions and methods for the inhibition of cancer metastasis.

12 Claims, 21 Drawing Sheets

OTHER PUBLICATIONS

Kawashima, H., Hirose, M., Hirose, J., Nagakubo, D., Plaas, A. H., and Miyasaka, M. 2000. Binding of a large chondroitin sulfate/dermatan sulfate proteoglycan, versican, to L-Selectin, P-Selectin, and CD44. J Biol Chem, 275: 35448-35456.

Cosgrove, R. H., Zacharski, L. R., Racine, E., and Andersen, J. C. 2002. Improved cancer mortality with low-molecular-weight heparin treatment: a review of the evidence. Semin Thromb Hemost, 28: 79-87.

Nelson, R. M., Cecconi, O., Roberts, W. G., Aruffo, A., Linhardt, R. J., and Bevilacqua, M. P. 1993. Heparin oligosaccharides bind L- and P-Selectin and inhibit acute inflammation. Blood, 82: 3253-3258.

Borsig, L., Wong, R., Hynes, R. O., Varki, N. M., and Varki, A. 2002. Synergistic effects of L- and P-Selectin in facilitating tumor metastasis can involve non-mucin ligands and implicate leukocytes as enhancers of metastasis. Proc Natl Acad Sci USA, 99: 2193-2198.

Wei, M., Tai, G., Gao, Y., Li, N., Huang, B., Zhou, Y., Hao, S., and Zeng, X. 2004. Modified heparin inhibits P-Selectin-mediated cell adhesion of human colon carcinoma cells to immobilized platelets under dynamic flow conditions. J Biol Chem, 279: 29202-29210.

Ma, Y. Q. and Geng, J. G. 2000. Heparan sulfate-like proteoglycans mediate adhesion of human malignant melanoma A375 cells to P-Selectin under flow. J Immunol, 165: 558-565.

Nazaruk RA, Rochford R, Hobbs MV, Cannon MJ. 1998. Functional diversity of the CD8+ T cell response to Epstein-Barr virus: Implications for the pathogenesis of EBV-associated lymphoproliferative disorders. Blood 91:3875-83.

Miller, V.M. et al. 2004, Targeting Alzheimer's disease genes with RNA interference: an efficient strategy for silencing mutant alleles. Nucleic Acids Res. 32:661-668.

McManus, MT et al., 2002, Gene silencing in mammals by small interfering RNAs. Nature Rev. Genet. 3:737-747.

Miller, VM et al., 2003, Allele-specific silencing of dominant disease genes Proc. Natl. Acad. Sci. USA 100:7195-7200.

Kitagawa, H et al. 2003, Molecular cloning of a chondroitin polymerizing factor that cooperates with chondroitin synthase for chondroitin polymerization. J. Biol. Chem. 278:23666-23671.

Sugahara, K et al., 2003, Recent advances in the structural biology of chondroitin sulfate and dermatan sulfate. Current Opinion in Structural Biology 13:612-620.

Yu, N. and M. Wang., 2008, Anticancer drug discovery targeting DNA hypermethylation. 15:135-1375.

* cited by examiner

A. Secondary Antibody

B. P-selectin

C. P-selectin + heparinase

D. P-selectin +chondroitinase

E. P-selectin + chondroitinase and heparinase

SEQUENCE LISTING

<160> NUMBER OF SEQ ID NOS: 2

<210> SEQ ID NO 1
<211> LENGTH: 31
<212> TYPE: DNA
<213> ORGANISM: Artificial
<220> FEATURE:
<223> OTHER INFORMATION: PCR primer

<400> SEQUENCE: 1
cgagaattct caggtgaacc aagccgctat g          31

<210> SEQ ID NO 2
<211> LENGTH: 27
<212> TYPE: DNA
<213> ORGANISM: artificial
<220> FEATURE:
<223> OTHER INFORMATION: PCR primer

<400> SEQUENCE: 2
cgactcgaga tggatcccct gggtgca          27

INHIBITION OF CANCER METASTASIS

CROSS-REFERENCES TO RELATED APPLICATIONS

This application claims the benefit and priority as a continuation-in-part application of U.S. Utility patent application Ser. No. 11/694,370, filed Mar. 30, 2007, which claims priority from U.S. Provisional application No. 60/788,018 filed on Mar. 31, 2006, the contents of both of which are incorporated herein by reference in their entirety.

STATEMENT REGARDING FEDERALLY SPONSORED RESEARCH

This invention was made with government support under grant DAMD 17-0101-0366 awarded by Department of Defense and grant CA089480 awarded by the National Institutes of Health. The government has certain rights in this invention.

BACKGROUND OF THE INVENTION

Cancer metastasis is strongly correlated with a poor prognosis of patients. The multi-step process of metastasis includes release of malignant cells from the primary neoplasm, migration of cancer cells into circulation, adhesion at distant sites, and growth of the disseminated cancer cells within the vessels or within the tissue following extravasation. Each step in this process requires different types of interaction between cancer cells and the host microenvironment.

The selectin family of adhesion molecules include P-Selectin, L-Selectin, and E-Selectin. P-Selectin is a 140 kDa protein that is commonly expressed on the surface of a variety of cell types, including, but not limited to, platelets and endothelium. (See, for example, GenBank Accession No. P16109 (*Homo sapiens*) or GenBank Accession No. AAA40008 (*Mus musculus*).) E-Selectin is commonly expressed in a variety of cell types, including, for example, vascular endothelium. (See, for example, NP_000441 (*Homo sapiens*) or AAA37577 (*Mus musculus*).) L-selectin is expressed on lymphocytes.

Cell surface proteoglycans (PGs) are another class of cell surface adhesion molecules. These PGs may comprise glycosaminoglycan (GAG) side chains covalently bound to a protein core. The GAG side chain can be heparin sulfate (HS) or chondroitin sulfate (CS).

The mammary cell line 4T1 is a model system of spontaneous breast cancer metastasis. This model exhibits a deficiency in the oligosaccharides sialyl Lewis X (sLe$^x$) and sialyl Lewis A (sLe$^a$). This deficiency results in diminished homotypic adhesion and higher motility of the tumor cells.

BRIEF SUMMARY OF THE INVENTION

The present inventors demonstrate that P-Selectin binds to chondroitin sulfate proteoglycans on the surface of cancer cells. Additionally, the present inventors demonstrate that platelets which express P-Selectin bind to chondroitin sulfate proteoglycans on the surface of cancer cells through the P-Selectin molecule. The inventors further demonstrate that endothelial cells which express P-Selectin bind to chondroitin sulfate proteoglycans on the surface of cancer cells through the P-Selectin molecule. More importantly, the inventors demonstrate that inhibition of the aforementioned P-Selectin binding to chondroitin sulfate proteoglycans prevents metastasis by preventing tumor cell interaction with platelets or tumor cell interaction with endothelial cells at secondary sites. Inhibition of the interaction of tumor cell chondroitin sulfate proteoglycans with platelets or endothelium may be achieved in multiple ways as set forth herein.

In certain embodiments of the present invention, compositions are disclosed for the inhibition of cancer metastasis. In particular embodiments, such a composition for inhibiting metastasis of a cancer cell may comprise a chondroitin sulfate ligand. In further embodiments, such a composition for inhibiting metastasis of a cancer cell may comprise a P-Selectin ligand. In yet further embodiments, such a composition for inhibiting metastasis of a cancer cell may comprise an inhibitor of synthesis of chondroitin sulfate or sulfation of chondroitin sulfate.

In various embodiments of the present invention, methods of inhibiting metastasis are disclosed. In one embodiment, a method of inhibiting metastasis comprises blocking the interaction of a first cell comprising chondroitin sulfate with a second cell by contacting said first cell with a chondroitin sulfate ligand.

In another embodiment of the present invention, a method of inhibiting metastasis may comprise blocking the interaction of a first cell comprising chondroitin sulfate with a second cell comprising P-Selectin by contacting said second cell with a P-Selectin ligand.

In particular embodiments of the present invention, a method of inhibiting metastasis may comprise contacting a cancer cell with a chondroitin sulfate synthesis inhibitor or a chondroitin sulfate sulfation inhibitor.

Another embodiment of the invention provides a method of identifying a candidate drug to treat cancer comprising: testing one or more compounds for inhibiting a chondroitin sulfate synthesis enzyme to identify a compound that inhibits a chondroitin sulfate synthesis enzyme; wherein a compound that inhibits a chondroitin sulfate synthesis enzyme is a candidate drug to treat cancer.

Another embodiment of the invention provides a method of identifying a candidate drug to inhibit mestastasis comprising: (a) testing one or more compounds for binding to Melanoma Chondroitin Sulfate Proteoglycan, Syndecan-1, Syndecan-4, or Neuropilin-1 to identify a compound that binds to Melanoma Chondroitin Sulfate Proteoglycan, Syndecan-1, Syndecan-4, or Neuropilin-1; wherein a compound that binds to Melanoma Chondroitin Sulfate Proteoglycan, Syndecan-1, Syndecan-4, or Neuropilin-1 is a candidate drug to treat cancer.

Another embodiment of the invention provides a method of inhibiting metastasis in a mammal afflicted with cancer or suspected to be afflicted with cancer comprising: (a) administering to the mammal an antibody against, or T cells that specifically recognize, Melanoma Chondroitin Sulfate Proteoglycan (MCSP), Syndecan-1, Syndecan-4, or Neuropilin-1; or (b) vaccinating the mammal with MCSP, Syndecan-1, Syndecan-4, Neuropilin-1, or a peptide thereof.

Another embodiment of the invention provides a method of screening for an agent to inhibit cancer metastasis comprising: testing one or more compounds not previously known to treat cancer for effect on methylation of DNA to identify an agent that causes hypermethylation of DNA; testing the agent for inhibition of cancer metastasis in vivo in a mammal.

Another embodiment provides a method of treating breast cancer comprising: (a) administering to a patient an antibody against, or T cells that specifically recognize, Melanoma Chondroitin Sulfate Proteoglycan; or (b) vaccinating a patient with Melanoma Chondroitin Sulfate Proteoglycan or a peptide thereof.

Another embodiment provides a method of inhibiting metastasis in a mammal afflicted with cancer or suspected to be afflicted with cancer comprising: (a) administering to the mammal an antibody against, or T cells that specifically recognize, Syndecan-4; or (b) vaccinating the mammal with Syndecan-4 or a peptide thereof.

BRIEF DESCRIPTION OF THE DRAWINGS

FIG. 1A illustrates analysis of 4T1-EGFP, cells incubated with fluorescein isothiocyanate (FITC) conjugated secondary antibody. FIG. 1B illustrates analysis of 4T1-FTIII cells incubated with FITC-conjugated secondary antibody. FIG. 1C illustrates analysis of 4T1-EGFP cells incubated with FH6 primary antibody followed by FITC-conjugated secondary antibody. FIG. 1D illustrates analysis of 4T1-FTIII cells incubated with FH6 primary antibody followed by FITC-conjugated secondary antibody. FIG. 1E illustrates analysis of 4T1-EGFP cells incubated with KM93 primary antibody followed by FITC-conjugated secondary antibody. FIG. 1F illustrates analysis of 4T1-FTIII cells incubated with KM93 primary antibody followed by FITC-conjugated secondary antibody. FIG. 1G illustrates analysis of 4T1-EGFP cells incubated with CSLEX1 primary antibody followed by FITC-conjugated secondary antibody. FIG. 1H illustrates analysis of 4T1-FTIII cells incubated with CSLEX1 primary antibody followed by FITC-conjugated secondary antibody.

FIG. 3A illustrates 4T1 cells stained with human IgG as a control. FIG. 3B illustrates IgG-chimeric E-Selectin binding in the absence of EDTA. FIG. 3C illustrates IgG-chimeric E-Selectin binding in the presence of 10 mM EDTA. FIG. 3D illustrates IgG-chimeric P-Selectin binding in the absence of EDTA. FIG. 3E illustrates IgG-chimeric P-Selectin binding in the presence of 10 mM EDTA. FIG. 3F illustrates IgG-chimeric P-Selectin binding in the presence of 20 mM EDTA. FIG. 3G illustrates IgG-chimeric P-Selectin binding in the presence of 40 mM EDTA. Mean fluorescence intensity for each histogram is shown.

FIG. 6A illustrates P-Selectin binding to untreated cells. FIG. 6B illustrates P-Selectin binding to cells treated to inhibit sulfation.

FIG. 7A illustrates untreated cells. FIG. 7B illustrates P-Selectin binding to untreated cells. FIG. 7C illustrates P-Selectin binding to cells treated with heparinase and chondroitinase.

FIG. 10A illustrates the tumor cells incubated with secondary antibody alone. FIG. 10B illustrates the interaction of P-Selectin with the tumor cells when the P-Selectin had been pre-incubated with 0.7 Units heparin prior to exposure to the cells. FIG. 10C illustrates the interaction of P-Selectin with the tumor cells when the P-Selectin had been pre-incubated with 3.0 Units heparin prior to exposure to the cells. FIG. 10D illustrates the interaction of P-Selectin with the tumor cells when the P-Selectin had been pre-incubated with 15.0 Units heparin prior to exposure to the cells. FIG. 10E illustrates the interaction of P-Selectin with the tumor cells when the P-Selectin had been pre-incubated with 60.0 Units heparin prior to exposure to the cells. FIG. 10F illustrates the interaction of P-Selectin with the tumor cells when the P-Selectin had been pre-incubated with 120.0 Units heparin prior to exposure to the cells.

FIG. 11A illustrates lack of binding of 4T1 cells incubated with untreated platelets. FIG. 11B illustrates binding of 4T1 cells to platelets which had been pre-treated with thrombin. FIG. 11C illustrates that heparin can inhibit binding of 4T1 cells to platelets which had been pre-treated with thrombin.

FIG. 12A illustrates 4T1 cells incubated with secondary antibody alone. FIG. 12B illustrates P-Selectin binding to 4T1 cells. FIG. 12C illustrates P-Selectin binding to 4T1 cells which had been pre-treated with heparinase. FIG. 12D illustrates P-Selectin binding to 4T1 cells which had been pre-treated with chondroitinase. FIG. 12E illustrates P-Selectin binding to 4T1 cells which had been pre-treated with both heparinase and chondroitinase.

FIG. 13 illustrates inhibition of P-Selectin binding to 4T1 cells by chondroitin sulfate.

FIG. 14A illustrates 4T1 cells incubated with secondary antibody alone. FIG. 14B illustrates P-Selectin binding to 4T1 cells. FIG. 14C illustrates P-Selectin binding to 4T1 cells when the P-Selectin had been pre-treated with 0.5 mg/ml chondroitin sulfate E. FIG. 14D illustrates P-Selectin binding to 4T1 cells when the P-Selectin had been pre-treated with 0.05 mg/ml chondroitin sulfate E. FIG. 14E illustrates P-Selectin binding to 4T1 cells when the P-Selectin had been pre-treated with 0.005 mg/ml chondroitin sulfate E. FIG. 14F illustrates P-Selectin binding to 4T1 cells when the P-Selectin had been pre-treated with 0.0005 mg/ml chondroitin sulfate E.

FIG. 15A illustrates MDA-MET cell variant, which is a bone-colonizing variant of MDA-MB-231 cell line, incubated with secondary antibody alone. FIG. 15B illustrates P-Selectin binding to MDA-MET cells. FIG. 15C illustrates P-Selectin binding to MDA-MET cells when the cells had been pre-treated with heparinase. FIG. 15D illustrates P-Selectin binding to MDA-MET cells when the cells had been pre-treated with chondroitinase. FIG. 15E illustrates P-Selectin binding to MDA-MET cells when the cells had been pre-treated with both heparinase and chondroitinase. FIG. 15F illustrates P-Selectin binding to MDA-MET cells when the P-Selectin had been pre-treated with 10.0 mg/ml of a chondroitin sulfate and glycosaminoglycan mixture. FIG. 15G illustrates P-Selectin binding to MDA-MET cells when the P-Selectin had been pre-treated with 1.0 mg/ml of a chondroitin sulfate and glycosaminoglycan mixture.

DETAILED DESCRIPTION

Definitions

Figure 1:
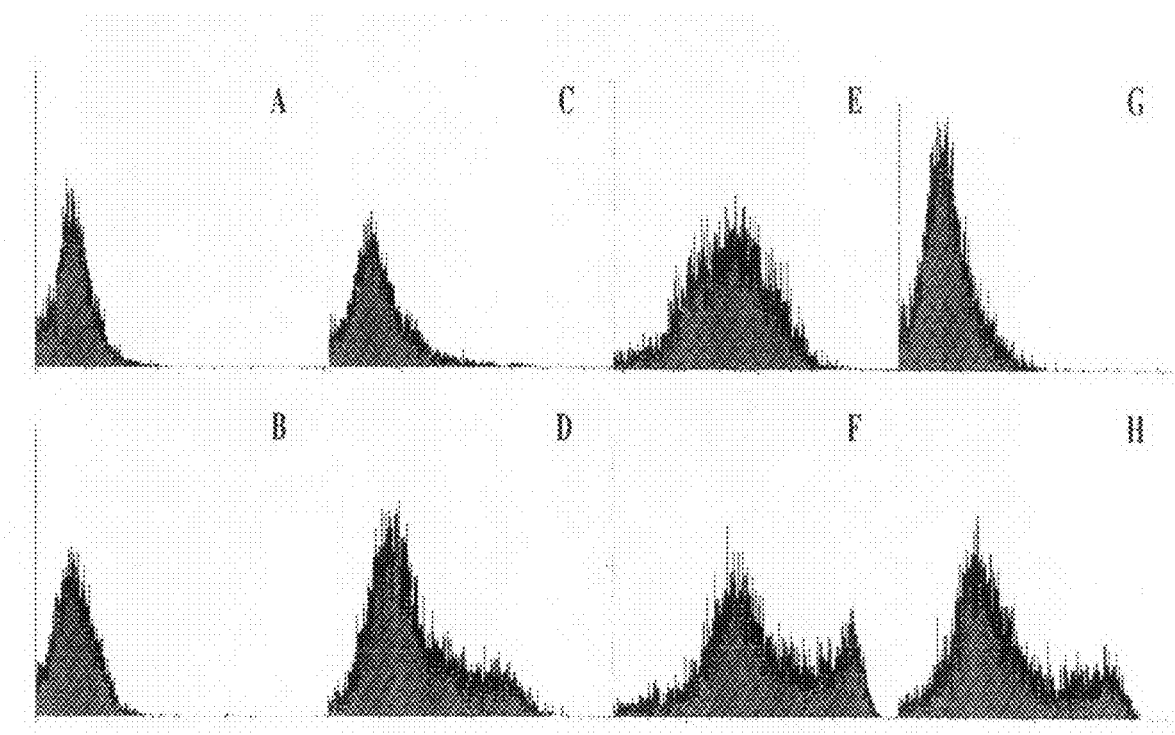
FIG. 1 illustrates flow cytometry analysis of anti-sialyl Lewis X monoclonal antibody (FH6, KM93, or CSLEX) binding to 4T1 cells transfected with either vector alone (4T1-EGFP) or transfected with vector containing a DNA insert which expresses fucosyl-transferase III (4T1-FTIII).

T cells are considered to specifically recognize a protein or a particular sequence if the CD4+ or CD8+ T cells show a response when contacted with antigen-presenting cells or target cells pulsed with a peptide consisting of the sequence. The response may be cytolysis of target cells pulsed with the peptide consisting of the sequence, or cytokine release or amplification in response to contacting antigen-presenting cells pulsed with the peptide consisting of the sequence.
Description:

In certain embodiments of the present invention, compositions are disclosed for the inhibition of cancer metastasis. In particular embodiments, such a composition for inhibiting metastasis of a cancer cell may comprise a chondroitin sulfate ligand. In other embodiments, a composition for inhibiting metastasis of a cancer cell may comprise a P-Selectin ligand.

The compositions are pharmaceutical compositions and may comprise a pharmaceutically acceptable diluent. The pharmaceutical composition may be formulated for administration by any suitable route, including intravenous, subcutaneous, intramuscular, or intraperitoneal injection. The pharmaceutical compositions may also be formulated for oral administration.

CS proteoglycans on the surface of cancer cells are shown to be major P-Selectin ligands involved in prometastatic heterotypic adhesion of tumor cells to platelets or endothelial cells. Metastasis may be inhibited by contacting platelets or endothelial cells with a P-Selectin ligand thereby preventing the interaction of platelets or endothelial cells with cancer cells. Thus, one aspect of the present invention provides for a metastasis inhibiting composition comprising a P-Selectin ligand that blocks the binding of P-Selectin to chondroitin sulfate on cancer cells. Such a P-Selectin ligand may be, for example, chondroitin sulfate.

One aspect of the present invention provides for a metastasis inhibiting composition comprising chondroitin sulfate. Yet a further aspect of the present invention provides for a metastasis inhibiting composition comprising a chondroitin sulfate binding agent which blocks the binding of P-Selectin to chondroitin sulfate. The particular CS that may be useful according to the present embodiment may be any of a variety of CS molecules including, but not limited to, CS PGs, CS A, CS B, CS C, CS D, or CS E. Additionally, inhibition of binding of platelets comprising P-Selectin to cancer cells which comprise cell surface CS PGs can be achieved by contacting the P-Selectin on platelets with free or unbound CS thereby inhibiting metastasis. Similarly, binding of endothelial cells comprising P-Selectin to cancer cells which comprise cell surface CS PGs can be blocked by contacting the P-Selectin on endothelial cells with free or unbound CS thereby inhibiting metastasis. The free or unbound chondroitin sulfate may be free or unbound CS PGs, CS A, CS B, CS C, CS D, or CS E.

In a further aspect of the present invention, binding of P-Selectin to CS PGs on the surface of cancer cells can be prevented by contacting the CS on cancer cells with a chondroitin sulfate ligand or binding agent. Free or unbound P-Selectin or a chondroitin sulfate binding domain of P-Selectin may be contacted to the cancer cell. In this manner, the free P-Selectin or chondroitin sulfate binding domain of P-Selectin may bind to the chondroitin sulfate of the cancer cells and prevent the interaction of cancer cells with cells comprising P-Selectin, such as platelets or endothelium. Because the chondroitin sulfate of the cancer cells is bound, metastasis is inhibited.

The extent of synthesis of chondroitin sulfate and sulfation of chondroitin sulfate is relevant to the binding of chondroitin sulfate to P-Selectin. Therefore, in certain embodiments of the present invention, a composition for inhibiting metastasis of a cancer cell may comprise an inhibitor of synthesis chondroitin sulfate. Such an inhibitor would include an inhibitor of sulfation of chondroitin sulfate. By decreasing the synthesis or sulfation of chondroitin sulfate on tumor cells, the binding of chondroitin sulfate by P-Selectin is limited. As a result, it is possible to limit the metastasis of a cancer cell by inhibiting sulfation of chondroitin sulfate.

In various embodiments of the present invention, methods of inhibiting metastasis are disclosed. In one embodiment, a method of inhibiting metastasis comprises blocking the interaction of a first cell comprising chondroitin sulfate with a second cell by contacting said first cell with a chondroitin sulfate ligand.

In another embodiment of the present invention, a method of inhibiting metastasis may comprise blocking the interaction of a first cell comprising chondroitin sulfate with a second cell comprising P-Selectin by contacting said second cell with a P-Selectin ligand.

In various aspects of the present invention, methods are disclosed to inhibit metastasis by inhibiting the interaction of P-Selectin expressed on platelets or endothelium with chondroitin sulfate proteoglycans expressed on tumor cells.

In various aspects of the present invention, methods are disclosed to inhibit metastasis by inhibiting the interaction of P-Selectin expressed on endothelial cells with chondroitin sulfate proteoglycans expressed on tumor cells.

In yet another aspect of the present invention, binding of P-Selectin on platelets or P-Selectin on endothelial cells to CS PGs on the surface of cancer cells can be prevented by contacting the CS PGs on the surface of cancer cells with a chondroitin sulfate binding agent that inhibits or blocks the P-Selectin binding site. Such a chondroitin sulfate ligand or binding agent would be, such as, for example, free P-Selectin or such as, for example, anti-CS antibodies.

In a further aspect of the present invention, CS can be utilized to stimulate an immune response, thereby inducing CS-specific antibodies that block the interaction of P-Selectin with CS bound to tumor cells. Antibodies for such a strategy may be generated in vivo or in vitro. Such antibodies inhibit metastasis via active immunization or passive immunization.

In particular embodiments of the present invention, a method of inhibiting metastasis may comprise contacting a cancer cell with a chondroitin sulfate synthesis or sulfation inhibitor. It is within the scope of the present invention that disruption of the enzymatic pathways that result in CS production or other cellular pathways that result in P-Selectin production may be useful for inhibiting the interaction of CS of tumor cells with P-Selectin of platelets or P-Selectin of endothelial cells thereby inhibiting metastasis. In particular, a method of inhibiting metastasis may comprise contacting a cancer cell with a chondroitin sulfate synthesis or chondroitin sulfate sulfation inhibitor. Such an inhibitor may inhibit sulfation of chondroitin sulfate, thereby inhibiting the effectiveness of P-Selectin binding to chondroitin sulfate. As a result, metastasis is inhibited. Exemplary inhibitors include inhibitors of cellular enzymes that are involved in the synthesis of chondroitin sulfate. Particular enzymes include, but are not limited to, chondroitin synthase, chondroitin N-acetylgalactosaminyltransferase (Chondroitin GalNAcT), chondroitinglucuronate C5-epimerase, chondroitin 4-O-sulfotransferase-1 (C4ST1), chondroitin 4-O-sulfotransferase-2 (C4ST2), chondroitin 4-O-sulfotransferase-3 (C4ST3), dermatan 4-O-sulfotransferase-1 (D4ST1), chondroitin 6-O-sulfotransferase (C6ST), chondroitin 6-O-sulfotransferase-2 (C6ST2), chondroitin 4-sulfate 6-O-sulfotransferase (GalNAc4S-6ST) and galactosaminyl uronyl 2-0 sulfotransferase (CS/DS2ST). Inhibition of any of these enzymes may be achieved by any of a variety of compositions and methods. For example, small molecule inhibitors of an enzyme may be used. Alternatively, the expression of particular enzymes may be down-regulated through molecular biology techniques that are commonly known to one of skill in the relevant art. For example, anti-sense RNAs from anti-sense constructs or siRNA (short interfering RNAs) may be used to disrupt translation and thereby inhibit expression.

It is within the scope of various aspects of this invention that metastasis may be inhibited for numerous cancers including, but not limited to, cancers selected from the group consisting of colon cancer, lung cancer, breast cancer, malignant melanoma, gastric cancer, tongue squamous cancer, myeloma and neuroblastoma.

In various aspects of the present invention, methods are disclosed to inhibit metastasis by inhibiting the interaction of P-Selectin expressed on platelets with chondroitin sulfate proteoglycans expressed on tumor cells. In various aspects of the present invention, methods are disclosed to inhibit metastasis by inhibiting the interaction of P-Selectin expressed on endothelial cells with chondroitin sulfate proteoglycans expressed on tumor cells.

In one aspect of the present invention, CS proteoglycans on the surface of cancer cells are shown to be major P-Selectin ligands involved in prometastatic heterotypic adhesion of tumor cells to platelets or endothelial cells. In another aspect of the present invention, metastasis may be inhibited by contacting platelets or endothelial cells with a P-Selectin ligand thereby preventing the interaction of platelets or endothelial cells with cancer cells.

In a further aspect of the present invention, binding of P-Selectin to CS PGs on the surface of cancer cells can be prevented by contacting the P-Selectin with free or unbound CS thereby inhibiting metastasis. Additionally, inhibition of binding of platelets or endothelium which comprise P-Selectin to cancer cells which comprise cell surface CS PGs can be achieved by contacting the P-Selectin on platelets with free or unbound CS. The free or unbound chondroitin sulfate may be free or unbound CS PGs, CS A, CS B, CS C, CS D, CS E.

In yet a further aspect of the present invention, binding of P-Selectin to CS PGs on the surface of cancer cells can be prevented by contacting the P-Selectin with a P-Selectin ligand, such as a small molecule, that prevents, blocks or inhibits binding of P-Selectin to CS thereby inhibiting metastasis. Additionally, inhibition of binding of platelets which comprise P-Selectin to cancer cells which comprise cell surface CS PGs can be achieved by contacting the P-Selectin on platelets with a P-Selectin ligand that prevents, blocks or inhibits binding of P-Selectin to CS, thereby inhibiting metastasis. Similarly, binding of endothelial cells which comprise P-Selectin to cancer cells which comprise cell surface CS PGs can be achieved by contacting the P-Selectin on endothelial cells with a P-Selectin ligand that prevents, blocks or inhibits binding of P-Selectin to CS thereby inhibiting metastasis. It is also envisioned within the scope of the present invention that modified forms of CS chains with improved specificity for P-Selectin or peptides that mimic the clustering structure of tumor cell surface CS may also be used for inhibition of metastasis.

It is within the scope of the various compositions and methods of this invention that metastasis may be inhibited for numerous cancers including, but not limited to, cancers selected from the group consisting of colon cancer, lung cancer, breast cancer, malignant melanoma, gastric cancer, tongue squamous cancer, myeloma and neuroblastoma. It also may be inhibited for other cancers, including but not limited to prostate cancer.

Another embodiment of the invention provides a method of identifying a candidate drug to treat cancer (or inhibit metastasis) comprising: testing one or more compounds for inhibiting a chondroitin sulfate synthesis enzyme to identify a compound that inhibits a chondroitin sulfate synthesis enzyme; wherein a compound that inhibits a chondroitin sulfate synthesis enzyme is a candidate drug to treat cancer (or inhibit metastasis).

In particular embodiments, the CS synthesis enzyme is selected from the group consisting of: chondroitin synthase, chondroitin N-acetylgalactosaminyltransferase (Chondroitin GalNAcT), chondroitin-glucuronate C5-epimerase, chondroitin 4-O-sulfotransferase-1 (C4ST1), chondroitin 4-O-sulfotransferase-2 (C4ST2), chondroitin 4-O-sulfotransferase-3 (C4ST3), dermatan 4-O-sulfotransferase-1 (D4ST1), chondroitin 6-O-sulfotransferase (C6ST), chondroitin 6-O-sulfotransferase-2 (C6ST2), chondroitin 4-sulfate 6-O-sulfotransferase (GalNAc4S-6ST) and galactosaminyl uronyl 2-0 sulfotransferase (CS/DS2ST).

In other particular embodiments, the CS synthesis enzyme is selected from the group consisting of: chondroitin synthase, chondroitin-glucuronate C5-epimerase, chondroitin 4-O-sulfotransferase-1 (C4ST1), chondroitin 4-O-sulfotransferase-2 (C4ST2), chondroitin 4-O-sulfotransferase-3 (C4ST3), chondroitin 6-O-sulfotransferase (C6ST), chondroitin 6-O-sulfotransferase-2 (C6ST2), chondroitin 4-sulfate 6-O-sulfotransferase (GalNAc4S-6ST) and galactosaminyl uronyl 2-0 sulfotransferase (CS/DS2ST).

In another embodiment, the chondroitin synthesis enzyme is chondroitin N-acetylgalactosaminyltransferase (Chondroitin GalNAcT), which is reported to transfer beta1,4-N-acetylgalactosamine (GalNAc) from UDP-[(3)H]GalNAc to a polymer chondroitin (beta-GalNAc transferase II activity. (Uyama T, Kitagawa H, Tamura Ji J, Sugahara K. Molecular cloning and expression of human chondroitin N-acetylgalactosaminyltransferase: the key enzyme for chain initiation and elongation of chondroitin/dermatan sulfate on the protein linkage region tetrasaccharide shared by heparin/heparan sulfate. J Biol. Chem. 2002 Mar. 15; 277(11):8841-6.)

In another embodiment, the chondroitin synthesis enzyme is dermatan 4-O-sulfotransferase-1 (D4ST1), works following the epimerase that makes cs-b. D4ST-1 is reported to transfer sulfate to GalNAc residues in -IdoUA-Gal-NAc-IdoUA- and -GlcUA-GalNAc-GlcUA- sequences.

Chondroitin 6-O-sulfotransferase (C6ST) (EC:2.8.2.17) catalyzes addition of a sulfate on carbon 6 of the NAcetylgalactosamine residues of chondroitin. Galactosaminyl uronyl 2-O-sulfotransferase (CS/DS2ST) oversulfates CS-B. Chondroitin 4-sulfate 6-O-sulfotransferase (GalNAc4S-6ST) (EC: 2.8.2.33) adds a sulfate to the 6 position of chondroitin 4-sulfate.

Key CS synthesis enzymes are listed in Tables 1 and 2.

TABLE 1

Chondroitin sulfate types and key enzymes in the pathway

| Chondroitin type product | Disaccharide repeat substrate | Modifying enzymes | |
|---|---|---|---|
| | | Sulfotransferase | Epimerase |
| A | [GlcUAβ1-3GalNAc(4S)] | Chondroitin-4 sulfotransferase 11, 12, 13 | — |
| B | [IdoUA(2S)α1-3GalNAc(4S)] | Uronyl-2-sulfotransferase and chondroitin-4 sulfotransferase 11, 12, 13 | dermatan sulfate epimerase |
| C | [GlcUAβ1-3GalNAc(6S)] | N-acetylglucosamine-6-O sulfotransferase 7 | — |
| D | [GlcUA(2S)β1-3GalNAc(6S)] | Uronyl-2-sulfotransferase and N-acetylglucosamine 6-O sulfotransferase 7 | — |
| E | [GlcUAβ1-3GalNAc(4S, 6S)] | Chondroitin-4 sulfotransferase 11, 12, 13 and N-acetylgalactosamine 4-sulfate 6-O-sulfotransferase | — |
| iE | [IdoUAα1-3GalNAc(4S, 6S)] | Chondroitin-4 sulfotransferase 11, 12, 13 and N-acetylgalactosamine 4-sulfate 6-O-sulfotransferase | dermatan sulfate epimerase |

TABLE 2

Genes involved in biosynthesis of human CS types.

| RefSeq Accession | Gene Name | Full Name | Enzyme |
|---|---|---|---|
| NM_018413 | CHST11 | Chondroitin 4-O-sulfotransferase 11 (C4ST1) | EC:2.8.2.5 |
| NM_018641 | CHST12 | Chondroitin 4-O-sulfotransferase 12 (C4ST2) | EC:2.8.2.5 |
| NM_152889 | CHST13 | Chondroitin 4-O-sulfotransferase 13 (C4ST3) | EC:2.8.2.5 |
| NM_004273 | CHST3 | Chondroitin 6-O-sulfotransferase 3 | EC:2.8.2.17 |
| NM_014918 | CHSY1 | Chondroitn synthase 1 | EC:2.4.1.175 EC:2.4.1.226 |
| NM_015892 | GALNAC4S-6ST | Chondroitin 4-sulafte 6-O-sulfotransferase | EC:2.8.2.33 |
| NM_013352 | SART2 or DS-epimerase | Squamous cell carcinoma antigen recognized by T cells 2 or Dermatan sulfate-5-epimerase | EC:5.1.3.19 |

It is shown below in Example 21 that CHST11, also known as C4ST1, is very highly expressed in highly aggressive breast cancer cells. This is further evidence linking chondroitin sulfate synthesis and in particular C4ST to metastasis. Thus, a compound that inhibits an enzyme in the pathway for synthesis of chondroitin sulfate is expected to inhibit metastasis.

Methods are known in the art to screen a library of compounds or individual compounds for inhibition of enzymes. One simple way to screen for inhibitors of chondroitin synthesis enzyme is to screen wells of a multiwell plate where each well is treated with a different compound, screening with an antibody against CS (see, e.g., Uyama, T. et al., J. Biol. Chem. 281:38668-38674). It is shown below in Example 14 that CS-B and CS-E inhibited P-Selectin binding to tumor cells more than CS-A and CS-C. Thus, it may be advantageous to screen with an antibody against CS-E or CS-B specifically.

Inhibition of particular enzymes involved in CS synthesis may be assayed in vitro with purified enzyme or crude extracts containing the enzyme of interest using appropriate radioactively labeled substrate. For instance, chondroitin-glucuronate C5-epimerase activity may be assayed using 5-$^3$H-labeled glucuronic acid residues and assaying for release of $^3$H$_2$O. (Li, J-P et al., 2001, J. Biol. Chem. 276: 20069-20077; Campbell, P. et al., 1994, J. Biol. Chem. 269: 26953-26958; Li, J. P. et al., 1997, J. Biol. Chem. 272:28158-28163.)

Chondroitin-glucuronate C5-epimerase is of particular interest because it is involved specifically in synthesis of CS-B.

Chondroitin 4-sulfate 6-O-sulfotransferase, also known as N-acetylgalactosamine 4-sulfate 6-O-sulfotransferase (GalNAc4S-6ST), transfers a sulfate from 3'-phosphoadenosine 5'-phosphosulfate (PAPS) to position 6 of N-acetylgalactosamine 4-sulfate in chondroitin sulfate. It can be assayed in an assay mixture with [$^{35}$S]PAPS and CS-A as substrates, assaying for $^{35}$S-labeled glycosaminoglycans (Ito, Y. et al., 2000, J. Biol. Chem. 275:34728-34736). GalNAc4S-6ST is of particular interest because it is involved specifically in synthesis of CS-E.

Antibodies are also available that are specific for different types of CS, e.g., CS-A, CS-E, and CS-B, which can be used to detect the products of the enzyme reactions in order to screen for inhibitors.

Another embodiment of the invention provides a method of identifying a candidate drug to inhibit mestastasis comprising: (a) testing one or more compounds for binding to Melanoma Chondroitin Sulfate Proteoglycan, Syndecan-1, Syndecan-4, or Neuropilin-1 to identify a compound that binds to Melanoma Chondroitin Sulfate Proteoglycan, Syndecan-1, Syndecan-4, or Neuropilin-1; wherein a compound that binds to Melanoma Chondroitin Sulfate Proteoglycan, Syndecan-1, Syndecan-4, or Neuropilin-1 is a candidate drug to treat cancer. The candidate drug should bind to MCSP, Syndecan-1, Syndecan-4, or Neuropilin-1 in their forms with CS attached to the protein.

In particular embodiments, the compound that binds one of the proteins is an antibody against the protein. Suitable antibodies may be polyclonal or monoclonal. They may be an antibody fragment. They may be humanized antibodies.

Methods of identifying compounds that bind to MCSP, Syndecan-1, Syndecan-4, or Neuropilin-1 are known to persons of skill in the art. One method is to immobilize MCSP, Syndecan-1, Syndecan-4, or Neuropilin-1 on a solid surface, and assay the ability of a test compound to compete with soluble P-Selectin for binding to the immobilized protein. This can be done with a labeled P-Selectin as described in the Examples below. Alternatively, a competitive binding assay can be done assaying competition of the test compound against binding of a polyclonal or monoclonal antibody specific for the immobilized protein.

In particular embodiments, the compound is a peptide of less than 100 amino acid residues. In other embodiments, it is a small molecule of molecular weight less than 3,000, which may be non-peptidyl.

In other specific embodiments, the compound is an antibody.

One embodiment of the invention provides a method of inhibiting metastasis in a mammal afflicted with cancer or suspected to be afflicted with cancer comprising: (a) administering to the mammal an antibody against, or T cells that specifically recognize, Melanoma Chondroitin Sulfate Proteoglycan (MCSP), Syndecan-1, Syndecan-4, or Neuropilin-1; or (b) vaccinating the mammal with MCSP, Syndecan-1, Syndecan-4, Neuropilin-1, or a peptide thereof.

Antibodies against MCSP, Syndecan-1, Syndecan-4, or Neuropilin-1 can be prepared as described below.

T cells can be amplified ex vivo as described below. Amplified T cells that specifically recognize a particular antigen (MCSP, Syndecan-1, Syndecan-4, or neuroplin-1) can be infused into a patient to mount a response against that antigen that inhibits metastasis.

Vaccinating a mammal with MCSP, Syndecan-1, Syndecan-4, Neuropilin-1, or a peptide thereof may involve vaccinating the mammal with the whole protein, or with a peptide of the protein. The peptide may be part of fusion protein with other sequences. The protein or peptide may be mixed with an adjuvant to enhance the immune response. Various adjuvants including Freund's complete or incomplete adjuvants are known in the art.

The protein or peptide may also be on antigen-presenting cells when it is used to vaccinate the mammal. The most active antigen-presenting cells are dendritic cells, whose preparation is described below.

Reducing expression of MCSP, Syndecan-1, Syndecan-4 or Neuropilin-1 is a means to reduce chondroitin sulfate on tumor cells. That is, without these proteins, there are fewer proteins to attach chondroitin sulfate to, and therefore fewer CS ligands on the cancer cell available to bind to P-Selectin. Expression of the proteins can be reduced by small interfering RNAs (siRNA) targeted to the genes for MCSP(NM_001897.4), Syndecan-1 (NM_001006946.1), Syndecan-4 (NM_002999.2), or Neuropilin-1 (NM_003873.5). Likewise, siRNA can target a gene for a CS synthesis enzyme. Vectors and techniques for gene siRNA silencing of genes are disclosed in (17-20).

Thus, one embodiment of the invention provides a method of treating cancer or inhibiting metastasis comprising: administering to a mammal afflicted with cancer a nucleic acid vector adapted to express an siRNA targeting MCSP, Syndecan-1, Syndecan-4, or Neurpolin-1.

Another embodiment of the invention provides a method of treating cancer or inhibiting metastasis comprising: administering to a mammal afflicted with cancer a nucleic acid vector adapted to express an siRNA targeting a gene for a CS synthesis enzyme.

Another embodiment of the invention provides a method of screening for an agent to inhibit cancer metastasis comprising: testing one or more compounds not previously known to treat cancer for effect on methylation of DNA to identify an agent that causes hypermethylation of DNA; testing the agent for inhibition of cancer metastasis in vivo in a mammal.

"Methylation" as used herein refers to methylation of the 5-carbon of cytosine on CpG dinucleotides in DNA by enzymatic means.

It is shown herein that expression of MCSP, Syndecan-1, Neuropilin-1, and C4ST are all under methylation control. That is, methylation reduces expression of these genes. Thus, although methylation is usually thought of as causing cancer or increasing the risk of cancer, in the case of these genes, hypermethylation reduces their expression, and thus reduces the metastatic potential of a cancer.

Thus, agents that increase methylation are expected to reduce expression of each of these proteins and thus reduce metastasis.

Agents that cause decreased methylation are known. These hypomethylating agents include aza-deoxycytidine, aza-cytidine, and aza-dCTP (available from Methylation, Ltd., Port Orange, Fla.).

Hypermethylating drugs are less well known. Instead anticancer research has focused on drugs that reduce methylation (Yu N, Wang M. Anticancer drug discovery targeting DNA hypermethylation. Curr Med Chem. 2008; 15(14):1350-75).

Methylation can be assayed as described in Patra S K, et al. 2002 (DNA methyltransferase and demethylase in human prostate cancer, Mol Carcinog. 2002, 33(3):163-71). Screening for agents that cause hypermethylation (which may be by inhibition of demethylating enzyme or activation of a methylating enzyme) can be done by testing for inhibition of methylation or demethylation as described in Patra S K, et al. 2002 (DNA methyltransferase and demethylase in human prostate cancer, Mol Carcinog. 2002, 33(3):163-71). In brief, cultured cells (e.g., cancer cell lines) are washed and broken in lysis buffer containing detergent. Protein is quantified and a constant amount of crude lysis extract is placed in each well of a multiwell plate. For assay of methylation, 20 µg protein is incubated for 2 hours at 37° C. with pol(dI-dC) or poly(dG-dC) substrate (15 µg) in reaction buffer with 2 µCi of $^3$H-labeled S-adenosylmethionine. The reaction is stopped by adding 300 µl of 1% SDS, 2 mM EDTA, 3% 4-aminosalicylate, 5% butanol, 125 mM NaCl, 0.25 mg/ml carrier salmon testis DNA, and 1 mg/ml proteinase K. Protein is extracted with 88% phenol, 12% m-cresol, and 0.1% 8-hydroxyquinoline. The reacted DNA template is recovered by ethanol precipitation from the aqueous phase. DNA is filtered on Whatman (GF/C) filters and washed with 5% trichloroacetic acid followed by 70% ethanol. Filters are counted by scintillation counting.

For the demethylation assay, 20-25 µg of poly(dI-dC) or poly(dG-dC) is labeled by inciuation with 100 µg of cancer cell extract with 10 µCi $^3$H-labeled S-adenosylmethionine overnight at 37° C. The reaction is terminated and nucleic acids are precipitated and dissolved in reaction buffer. Unincorporated radioactive substances are removed by chromatography through a NAP-5 (Amersham) column. Purified radioactive DNA is quantified radioactively, and 20,000 cpm is incubated with cell or tissue extracts and released radioactive $CH_3OH$ is counted as a measure of demethylase activity.

DNA methylation levels at CpG sites of specific genes can be quantified, using bisulfite genomic sequencing followed by methods of quantitative analysis for these sequences. (Leakey T I et al. A simple algorithm for quantifying DNA methylation levels on multiple independent CpG sites in bisulfite genomic sequencing electropherograms. Nucleic Acids Res. 2008 June; 36(11):e64. Thomassin H, Kress C, Grange T. MethylQuant: a sensitive method for quantifying methylation of specific cytosines within the genome. Nucleic Acids Res. 2004 Dec. 2; 32(21):e168.)

P-Selectin binding to CS ligands on cancer cells also reduces angiogenesis and tumor growth, in addition to reducing metastasis. Thus, the methods described herein, in addition to being methods for inhibiting metastasis, are methods to treat cancer, reduce tumor growth, or reduce tumor angiogenesis.

T Cell and Dendritic Cell Culture, Amplification, and Assay.

Dendritic cells can be cultured, and T cells can be cultured, activated, and assayed, as described in International Application PCT/US07/024,300.

Dendritic Cell and T Cell Culture.

Peripheral blood mononuclear cells are recovered from peripheral blood by gradient centrifugation (Lymphoprep; Greiner Bio-One, Longwood, Fla.).

For preparation of dendritic cells, peripheral blood mononuclear cells are placed in six-well plates (Costar, Cambridge, Mass.) at a concentration of $5 \times 10^6$ per well in AIM-V medium. After incubation for 2 to 3 hours at 37° C., nonadherent cells were removed from the culture and the medium was replaced with AIM-V plus 800 units/mL granulocyte macrophage colony-stimulating factor and 500 units/mL IL-4. On days 3 and 5, half the medium is removed and replaced with AIM-V plus 800 units/mL granulocyte macrophage colony-stimulating factor and 500 units/mL IL-4. A mix of maturation cytokines (1 µmol/L/mL prostaglandin E2, 1,000 units/mL tumor necrosis factor-α, and 500 units/mL IL-1β) is added on day 5 or 6. For stimulation of T cells specific for a peptide, mature dendritic cells are collected after maturation for 48 hours, and pulsed with 50 µg/mL of peptide for 2 hours in AIM-V at 37° C. The dendritic cells are then washed once with AIM-V medium and used for T cell stimulation at a peripheral blood mononuclear cell/dendritic cell ratio of 30:1. After 7 days, T cells were collected and restimulated with peptide-pulsed dendritic cells. After the second stimulation, CD8+ or CD4+ T cells may optionally be specifically purified and recovered by positive selection with anti-CD8 or anti-CD4 magnetic beads (Dynal Biotech, Brown Deer, Wis.). During the second and third T cell stimulation and passage, 50 to 100 units/mL IL-2 is added to the medium, and T cells are periodically fed (every 2-3 days) by changing 50% to 70% of the medium and addition of fresh IL-2. Further passaging of CD8+ T cell lines uses peptide-loaded autologous peripheral blood lymphocytes as antigen-presenting cells.

Cytotoxicity Assays.

Standard $^{51}$Cr-release assays are done as described previously (16). Autologous lymphoblastoid cell lines are pulsed with 50 µg/mL of appropriate target peptide, or left unpulsed. Lymphoblastoid cell lines are pulsed overnight with 50 µg/mL of peptide at 37° C. in AIM-V medium, whereas dendritic cells are pulsed with 50 µg/mL peptide for 48 hours during final maturation. Peptide-pulsed targets were then labeled with 50 µCi $Na_2[^{51}Cr]O_4$ for an additional hour and washed three times before use. Target cells were plated at $1 \times 10^4$ per well in 96-well round-bottomed plates with effector T cells.

Raising Antibodies

To generate antibodies, MCSP, Syndecan-1, Syndecan-4, or Neuropilin can be administered directly to a mammal, or the proteins or peptide fragments thereof can be coupled to a carrier protein. Suitable carrier proteins include keyhole limpet hemocyanin, bovine serum albumin, and ovalbumin. Methods of coupling to the carrier protein include single step glutaraldehyde coupling and other methods disclosed in Harlow, Ed et al., *Antibodies: a laboratory manual*, Cold Spring Harbor Laboratory (1988).

The immunogen is used to immunize a vertebrate animal in order to induce the vertebrate to generate antibodies. Preferably the immunogen is injected along with an adjuvant such as Freund's adjuvant, to enhance the immune response. Suitable vertebrates include rabbits, mice, rats, hamsters, goats, and chickens.

Hybridomas to synthesize monoclonal antibodies can be prepared by methods known in the art. See, for instance, Wang, H., et al., *Antibody Expression and Engineering*, Am. Chem. Soc., Washington, D.C. (1995). Polyclonal and monoclonal antibodies can be isolated by methods known in the art. See, for instance, id. and Harlow et al.

Native antibodies are tetramers of two identical light (L) chains and two identical heavy (H) chains. The L and H chains each have variable domains that are responsible for antigen recognition and binding. The variability in the variable domains is concentrated in the complementarity determining regions (CDRs).

An antibody that is contemplated for use in the present invention can be in any of a variety of forms, including a whole immunoglobulin, an antibody fragment such as Fv, Fab, and similar fragments, a single chain antibody that includes the CDR, and like forms, all of which fall under the broad term "antibody" as used herein.

The term "antibody fragment" refers to an antigen-binding portion of a full-length antibody. Antibody fragments can be as small as about 4 amino acids, about 10 amino acids, or about 30 amino acids or more. Some types of antibody fragments are the following:

(1) Fab is the fragment that contains a monovalent antigen-binding fragment of an antibody molecule. A Fab fragment can be produced by digestion of whole antibody with the enzyme papain to yield an intact light chain and a portion of one heavy chain. Two Fab fragments are obtained per whole antibody molecule.

(2) Fab' is the fragment of an antibody that can be obtained by treating whole antibody with pepsin, followed by reduction to yield an intact light chain and a portion of the heavy chain. Two Fab' fragments are obtained per whole antibody molecule. Fab' fragments differ from Fab fragments by the addition of a few residues at the carboxyl terminus of the heavy chain CH1 domain including one or more cysteines.

(3) F(ab')$_2$ is the fragment that can be obtained by digestion of whole antibody with pepsin, without reduction. F(ab')$_2$ is a dimer of two Fab' fragments held together by two disulfide bonds.

(4) Fv is the minimum antibody fragment that contains a complete antigen recognition and binding site. Fv consists of a dimer of one H and one L chain variable domain in a tight, non-covalent association ($V_H$-$V_L$ dimer). It is in this configuration that the three CDRs of each variable domain interact to define an antigen-binding site. Collectively, the six CDRs confer antigen binding specificity to the antibody. However, even a single vaiable domain (or half of an Fv comprising only three CDRs specific for an antigen) has the ability to bind antigen, although at a lower affinity than the complete binding site.

(5) A single chain antibody (SCA) is defined as a genetically engineered molecule containing the variable region of the light chain and the variable region of the heavy chain linked by a suitable polypeptide linker as a genetically fused single chain molecule.

The preparation of polyclonal antibodies is well known to those skilled in the art. See, for example, Coligan et al., in *Current Protocols in Immunology*, section 2.4.1 (1992). The preparation of monoclonal antibodies is likewise conventional. See, for example, Harlow et al., page 726.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, *Nature* 256:495 (1975), or may be made by recombinant methods, e.g., as described in U.S. Pat. No. 4,816,567. The monoclonal antibodies for use with the present invention may also be isolated from phage antibody libraries using the techniques described in Clarkson et al., *Nature* 352:624 (1991), as well as in Marks et al., *J. Mol. Biol.* 222:581 (1991). Another method involves humanizing a monoclonal antibody by recombinant means to generate antibodies containing human specific and recognizable sequences. See, for review, Holmes et al., *J. Immunol.* 158:2192 (1997) and Vaswani et al., *Annals Allergy, Asthma & Immunol.* 81:105 (1998).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l. Acad. Sci.* 81:6851 (1984)).

Methods of making antibody fragments are also known in the art (see, for example, Harlow and Lane, *Antibodies: a Laboratory Manual*, Cold Spring Harbor Laboratory, New York (1988)). Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using pepsin produces two monovalent Fab fragments and an Fc fragment directly. These methods are described, for example, in U.S. Pat. Nos. 4,036,945, and 4,331,647, and references contained therein.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker bridging the two V domains. Methods for producing sFvs are described, for example, by Whitlow et al., *Methods: a Companion to Methods in Enzymology*, 2:97 (1991); Bird et al., *Science* 242:423 (1988); Ladner et al., U.S. Pat. No. 4,946,778; and Pack et al., *Bio/Technology* 11:1271 (1993).

Another form of an antibody fragment is a peptide containing a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, 2:106 (1991).

The invention contemplates human and humanized forms of non-human (e.g., murine) antibodies. Such humanized antibodies are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., *Nature* 321:522 (1986); Reichmann et al., *Nature* 332:323 (1988); Presta, *Curr. Opinion Struct. Biol.* 2:593 (1992); Holmes et al., *J. Immunol.* 158:2192 (1997); and Vaswani et al., *Annals Allergy, Asthma & Immunol.* 81:105 (1998).

Antibodies of the invention can also be mutated to optimize their affinity, selectivity, binding strength or other desirable property. One method of mutating antibodies involves affinity maturation using phage display. Affinity maturation using phage display refers to a process described in Lowman et al., *Biochemistry* 30:10832 (1991); see also Hawkins et al., *J. Mol. Biol.* 254:889 (1992).

Pharmaceutical Compositions

The agents presented herein can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present agents may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the agents may be combined with one or more excipients and used in the form of ingestible tablets, buccal tablets, troches, capsules, elixirs, suspensions, syrups, wafers, and the like. Such compositions and preparations should contain at least 0.1% of agent. The percentage of the compositions and preparations may, of course, be varied and may conveniently be between about 2 to about 60% of the weight of a given unit dosage form. The amount of the agent in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the agent, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the agent may be incorporated into sustained-release preparations and devices.

The agents may also be administered intravenously or intraperitoneally by infusion or injection. Solutions of the agents can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active agent in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the anti-cancer agents of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

EXAMPLES

The following examples are further illustrative of the present invention, but it is understood that the invention is not limited thereto.

The monoclonal antibody KM-93 was purchased from Kamiya Biomedical, Seattle, Wash. The antibodies FH6 and CSLEX1 were purchased from GlycoTech, Gaithersburg, Md. FITC-conjugated and biotinylated goat anti-mouse IgG or goat anti-mouse IgM were purchased from Sigma.

The murine breast tumor cell line 4T1 was obtained from ATCC (Manassas, Va.). The 4T1 cell line, FTIII transfected 4T1 cell line and pIRES-EGFP transfected cell line was maintained in DMEM supplemented with 10% fetal bovine serum at 37° C. in sterile culture flasks.

The 1083 bp coding fragment of the human fucosyl transferase III (FTIII) gene (see GenBank Accession Nos. NP_000140 and U27328.1) in pcDNA3 plasmid was kindly provided by Dr. Insug O'Sullivan (University of Illinois). The coding sequence was further adapted for cloning between EcoRI and XhoI restriction sites by PCR using the following primers: 5'-cgagaattctcaggtgaaccaagccgctatg-3' (SEQ ID NO.: 1) and 5'-cgactcgagatggatccctgggtgca-3' (SEQ ID NO.: 2). The amplified fragment was digested with EcoRI and XhoI, purified and inserted into the Multiple Cloning Site (MCS) of pIRES-EGFP vector to make FTIII-pIRES-EGFP construct. (The pIRES-EGFP vector was obtained from BD Biosciences Clontech (Palo Alto, Calif.).) The 4T1 cells were then transfected with this construct or pIRES-EGFP vector alone using Lipofectamine™ 2000 (Invitrogen, Carlsbad, Calif.) transfection reagent. The pIRES-EGFP vector contains an internal ribosome entry site (IRES) between the MCS and the EGFP (enhanced green fluorescent protein) coding region. This allows the FTIII gene (cloned into the MCS) and the EGFP gene to be translated from a single bicistronic mRNA.

Unless specified otherwise, flow cytometry was conducted as follows. Acquisition and analysis of data was performed on an EPICS™XL™.flow cytometer (Beckman Coulter, Inc., Fullerton, Calif.). Cells were passed to new flasks 24 hours before measuring lectin binding. The subconfluent monolayer of cells was detached with Cellstripper (Mediatech, Inc. Herndon, Va.) and washed with Dulbecco's phosphate buffered saline with Ca++ and Mg++ (Mediatech, Inc. Herndon, Va.). Cells were transferred to FACS buffer (Dulbecco's Phosphate Buffered Saline, 1% BSA and 0.1% Sodium Azide), counted and diluted to ~1-2×10$^6$/ml. Monoclonal antibodies were added to a final concentration of 10 µg/ml. Cells were incubated on ice for 30 minutes, washed twice with FACS buffer, before the addition of FITC-conjugated streptavidin (2 µg/ml) for lectin analysis or FITC-conjugated goat anti-mouse immunoglobulin for monoclonal analysis. Cells were then washed and fixed with paraformaldehyde, before analysis by flow cytometry.

Recombinant E- and P-Selectin/Fc (human IgG) were purchased from R&D systems, Minneapolis, Minn. These recombinant molecules and FITC-conjugated anti-human IgG were used for binding analyses in flow cytometry assays. Human and murine recombinant selectins were used for human and murine cells, respectively.

All experiments were repeated at least three times. The Student's t-test or Fisher exact test was used to compare differences between means. Differences were considered significant if P was <0.05.

Example 1

4T1 cells are deficient in sLe$^a$ expression making the cell line a good candidate to study the involvement of sLe$^x$-mediated adhesion properties. There are several monoclonal antibodies (mAbs) defined as KM93, FH6 and CSLEX1 that recognize sLe$^x$. These mAbs recognize different forms of the sLe$^x$ antigen (1-3). FH6 is specific for an extended form of sLe$^x$ (4), while CSLEX1 and KM93 antibodies both recognize the sLe$^x$ tetrasaccharide. However, the nature of the molecules carrying the carbohydrate determinant is known to affect the reactivity of CSLEX1 and KM93 (5). Among the above antibodies, only KM93 reacts with the 4T1 tumor cell surface. KM93, CSLEX-1 or FH6 reactive sLe$^x$ epitopes may differentially react with P— and E-Selectin due to variations in lipid or peptide backbones.

The 4T1 cells were transfected with fucosyltransferase III (FTIII) to expand the expression of other sLe$^x$ epitopes (4T1-FTIII). The 4T1 cells were also transfected with pIRES-EGFP vector alone as a control (4T1-EGFP). FIGS. 1A and 1B illustrate 4T1-EGFP cells and 4T1-FTIII cells, respectively, incubated with secondary antibody alone as control. The binding of KM93 monoclonal antibody was increased on 4T1-FTIII cells (FIG. 1F) relative to 4T1-EGFP (FIG. 1E). More importantly, FH6 reactive epitopes were expressed at detectable levels in the 4T1-FTIII cells (FIG. 1D) compared to 4T1-EGFP cells (FIG. 1C). Also, CSLEX-1 reactive epitopes were expressed at detectable levels in the 4T1-FTIII cells (FIG. 1H) compared to 4T1-EGFP cells (FIG. 1G). The antibody binding data indicate that transfection with FTIII encoding sequence increased the expression of various sLe$^x$ epitopes.

Figure 2:
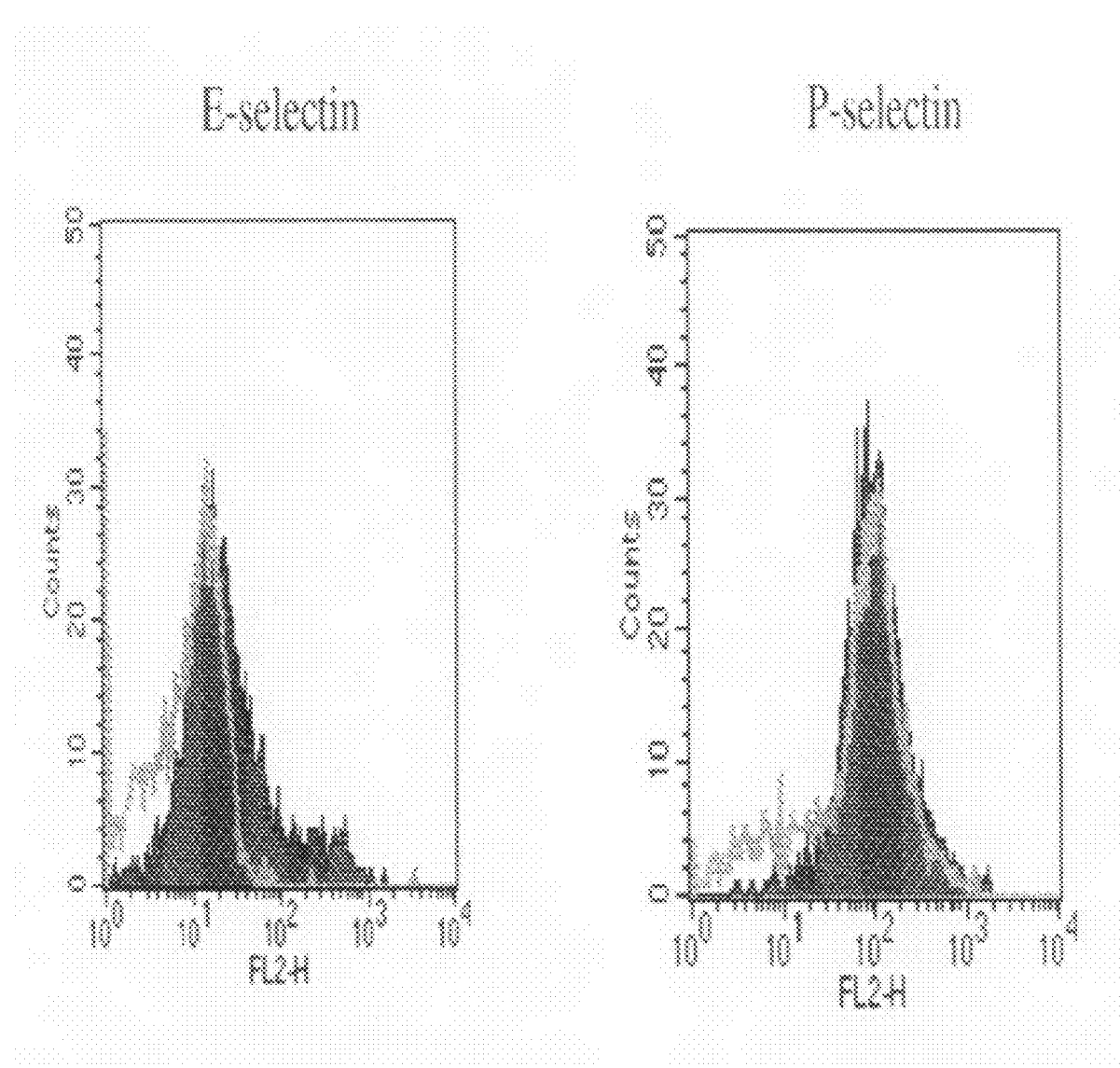
FIG. 2 illustrates E-Selectin and P-Selectin binding to 4T1 cells. Either 4T1-EGFP or 4T1-FTIII cells were first incubated with human IgG-chimeric E-Selectin or human IgG-chimeric P-Selectin and then stained with FITC-conjugated goat anti-human IgG. 4T1-EGFP cells are illustrated by open histograms and 4T1-FTIII cells are illustrated by filled histograms.

Example 2 is P-Selectin and E-Selectin reactivity with parental and transfected 4T1 cells were examined. Cells were incubated with recombinant mouse E-Selectin/Fc (human IgG) or P-Selectin/Fc (human IgG) chimeras and assayed for binding by flow cytometry. An increase for E-Selectin binding was observed after FT-III transfection (FIG. 2, first panel). This was expected given the increase in KM93, CSLEX-I and FH6 binding after transfection. P-Selectin, however, bound very well to the parental 4T1 cells and the binding did not increase for the transfected cells (FIG. 2, second panel). These data confirm that P-Selectin binding to 4T1 cells is not dependent on the expression sLe$^x$ on the tumor cell surface.

Example 3

Figure 3:
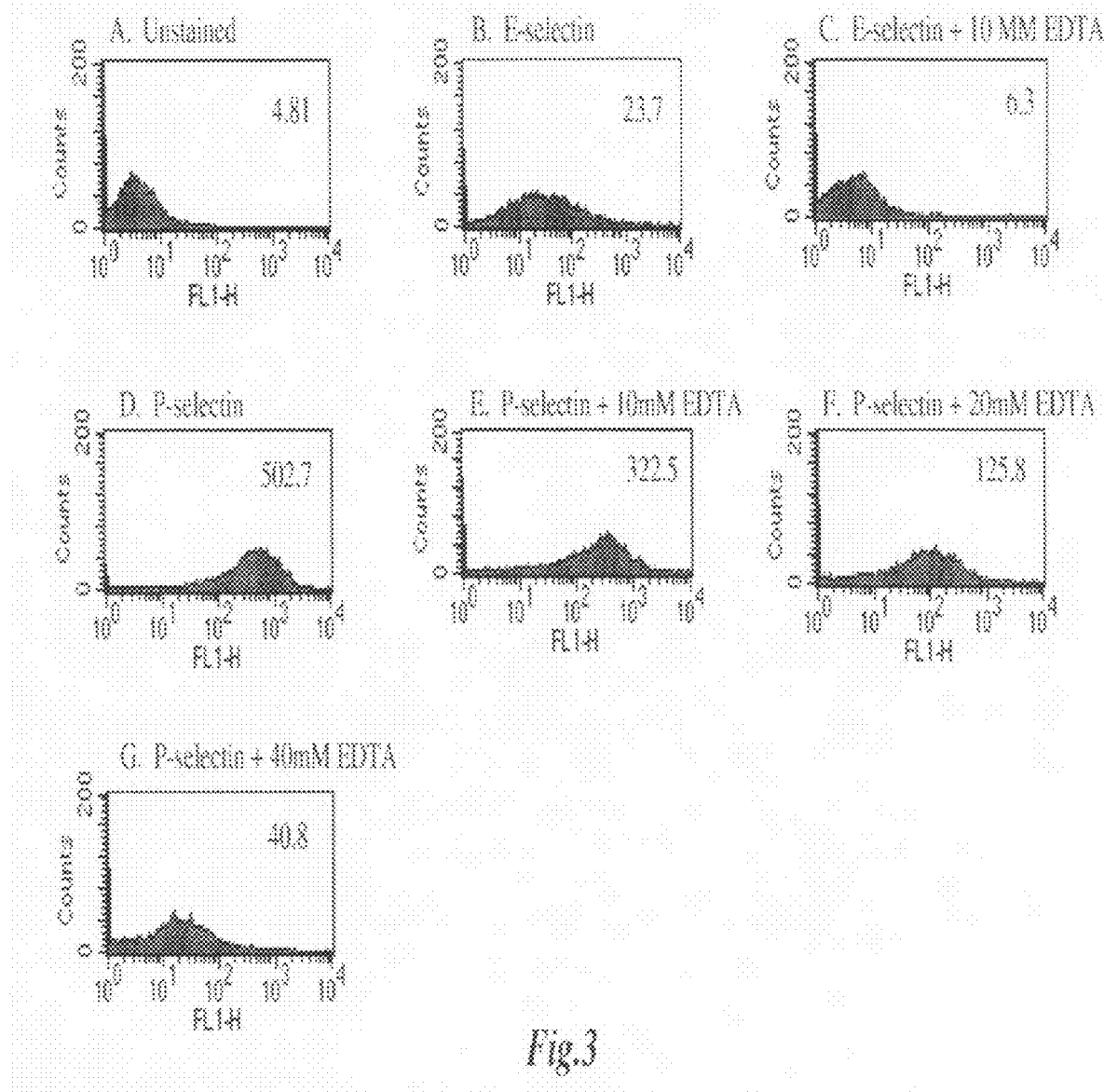
FIG. 3 illustrates calcium dependence of E-Selectin and P-Selectin binding to 4T1 cells.
Figure 4:
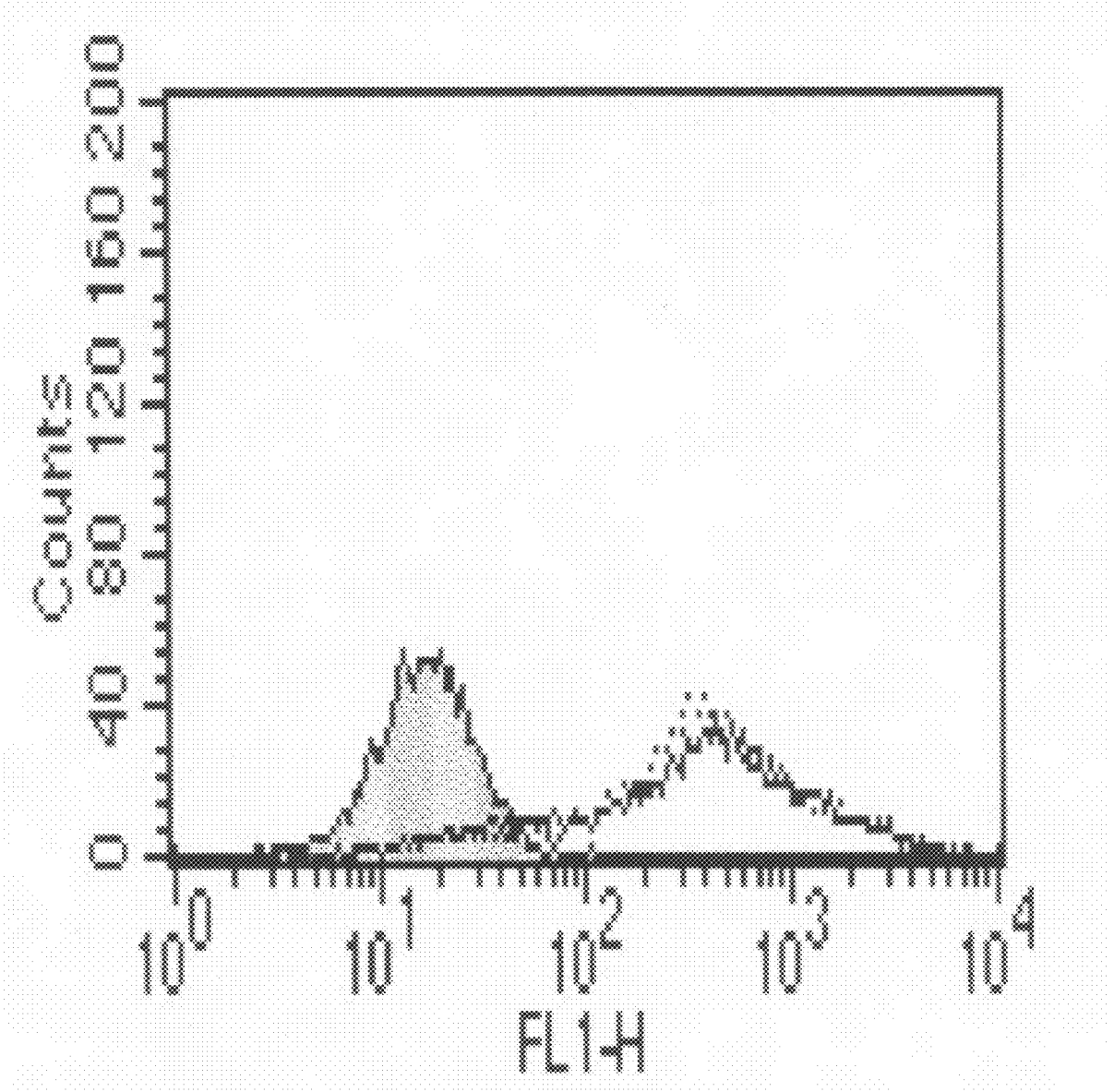
FIG. 4 illustrates the effect of neuraminadase treatment of 4T1 cells on P-Selectin binding. Filled histogram represents staining with secondary antibody only. Continuous line histogram represents P-Selectin reactivity without neuraminidase treatment. Dotted histogram represents P-Selectin reactivity with neuraminidase treatment.

The dependence of E-Selectin and P-Selectin binding to 4T1 cells on divalent cation concentration was examined. FIG. 3A illustrates unstained 4T1 cells. FIG. 3B illustrates 4T1 cells incubated with E-Selectin/Fc chimera followed by incubation with FITC-conjugated anti-human IgG. FIG. 3C is the same as FIG. 3B except the experiment was conducted in the presence of 10 mM EDTA. Both lectins bind the 4T1 cells, with P-Selectin showing very strong reactivity (FIG. 3D). Contrary to the E-Selectin reactivity (see FIGS. 3B and 3C), P-Selectin reactivity was not blocked by a low concentration of EDTA (see FIGS. 3D and 3E). EDTA inhibited P-Selectin reactivity only at high concentrations indicating the Ca$^{++}$-independent nature of the reactivity (see FIGS. 3F and 3G).

Example 4

Cells treated with neuraminidase show the relationship between sialylation and reactivity of P-Selectin. Neuraminidase (*Vibrio cholerae*) was purchased from Sigma (St. Louis, Mo.) and used at a concentration of 50 mU/ml. Neuraminidase treatment did not change the P-Selectin reactivity (FIG.

4). These results provide further evidence that E-Selectin and P-Selectin react with separate ligands on the surface of 4T1 cells. In contrast to E-Selectin, P-Selectin binds to unsialylated ligands on these cells in a $Ca^{2+}$-independent manner. Therefore, sialylated ligands are not a major ligand of P-Selectin in binding to the 4T1 cells.

Example 5

Figure 5:
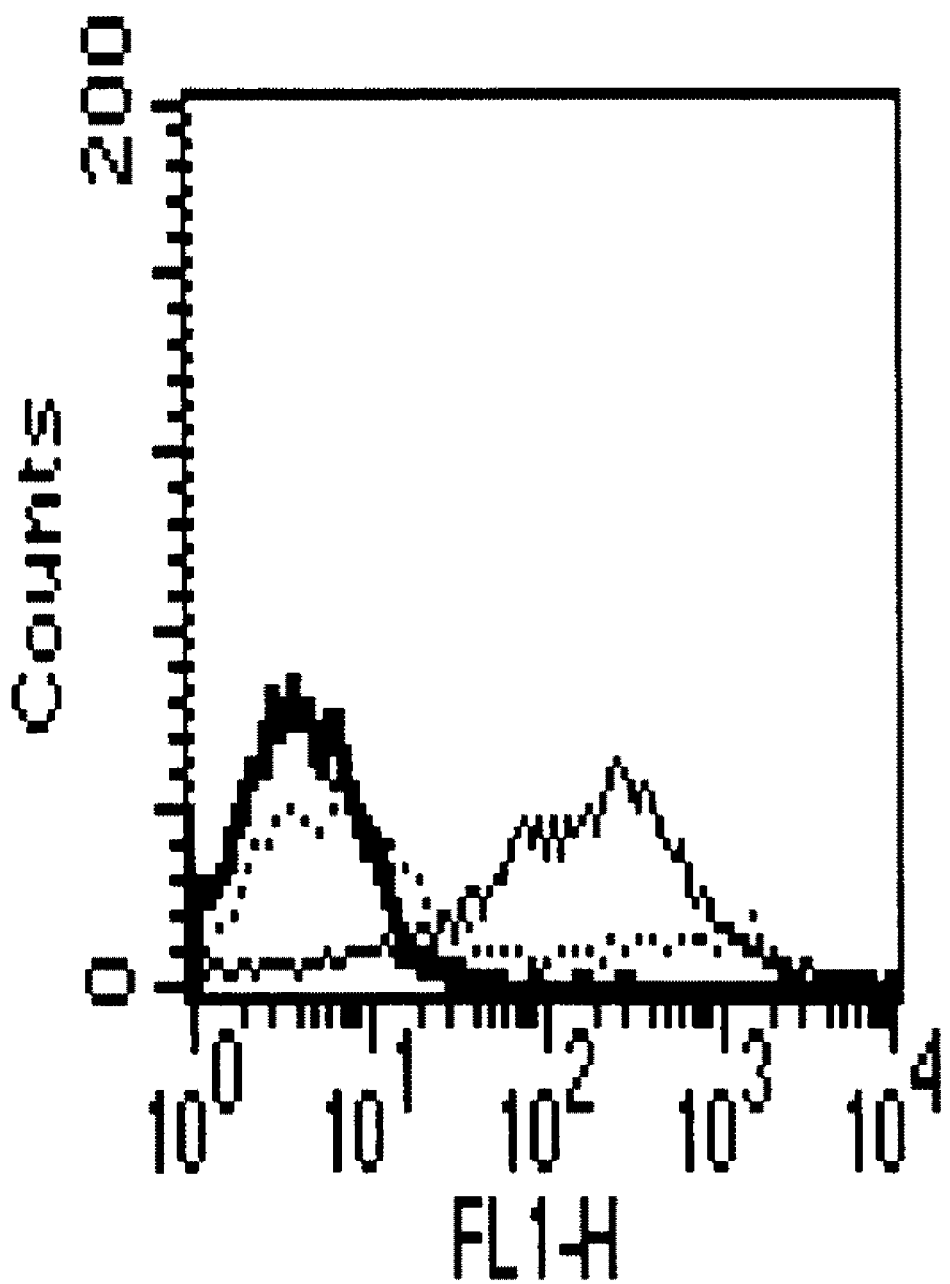
FIG. 5 illustrates that pronase treatment of 4T1 cells reduces P-Selectin reactivity with the cells. P-Selectin binding to the 4T1 cells (thin line histogram) was sharply reduced (dotted line) to the level of secondary antibody binding (thick solid line).

Cells (4T1) were treated with pronase to determine the proteinaceous nature of P-Selectin ligands. Treatment with pronase dropped the P-Selectin reactivity (dotted histogram) almost to the levels of the negative control (thick, solid line histogram), indicating the proteinaceous nature of the ligands (FIG. 5). The thin, solid line histogram represents P-Selectin binding to untreated cells.

Example 6

Figure 6:
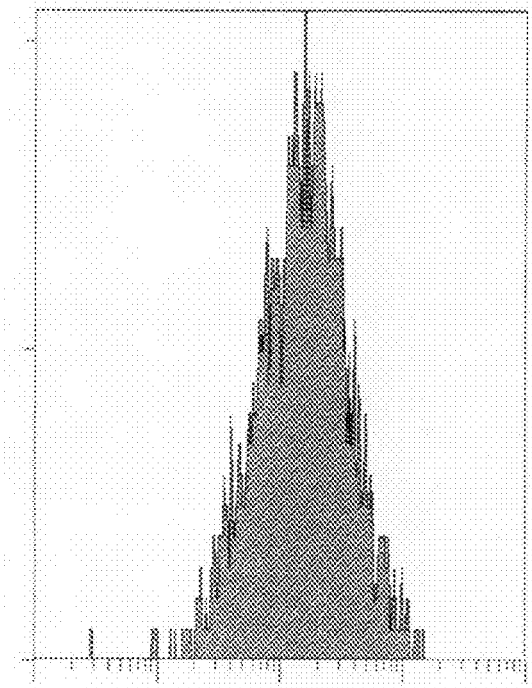
FIG. 6 illustrates that inhibition of sulfation decreases P-Selectin binding to 4T1 cells.
Figure 6:
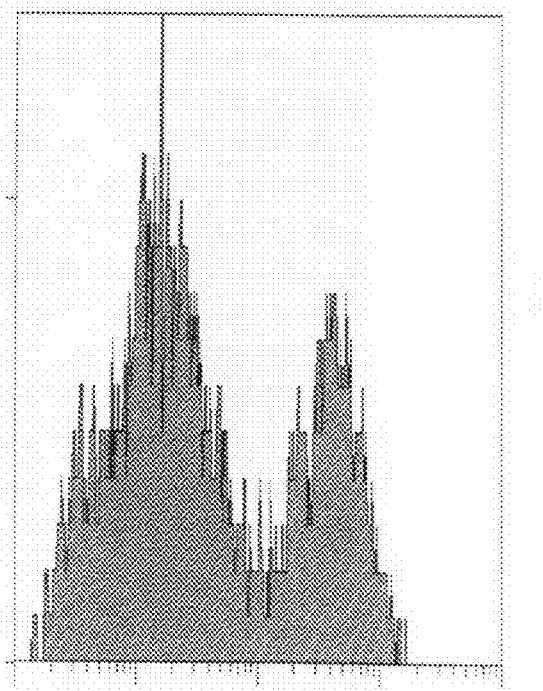

Sulfated glycosaminoglycans like heparan sulfate and chondroitin sulfate are carbohydrate moieties of proteoglycans, which serve as P-Selectin ligands (6, 7). The 4T1 cells were grown in sulfate-free medium in the presence of sodium chlorate to inhibit sulfate biosynthesis. Cells were washed with sulfate-free DMEM medium (Hyclone, Logan, Utah) supplemented with 10% dialyzed FBS and 100 mM sodium chlorate (Sigma) and cultured in the same medium for 2 hours. The medium was then refreshed and incubation was continued overnight. These treated cells were harvested with cell dissociation buffer (Gibco-Invitrogen. Carlsbad, Calif.), washed and resuspended in FACS buffer for further analyses by flow cytometry. Growing the cells in sulfate free medium containing sodium chlorate led to elimination of P-Selectin binding in a majority of the cells, indicating that most P-Selectin ligands on the 4T1 cells are sulfated (FIG. 6).

Example 7

Figure 7:
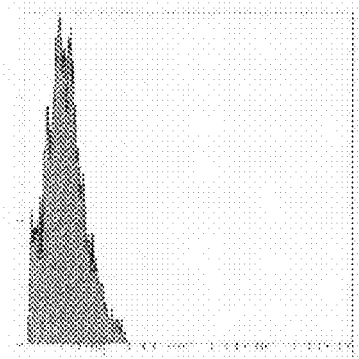
FIG. 7 illustrates the effect of heparinase and chondroitinase on P-Selectin binding.
Figure 7:
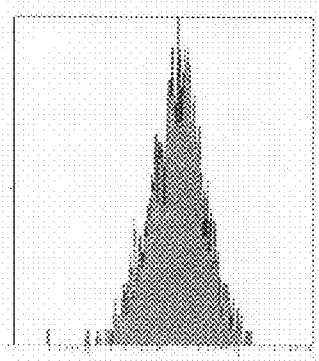
Figure 7:
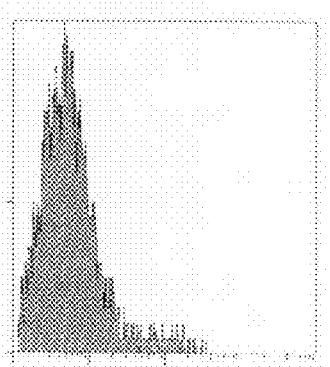

Treatment of 4T1 cells with a mixture of the glycosaminoglycan-cleaving enzymes, heparinase and chondroitinase, decreased P-Selectin binding (FIG. 7). Removal of glycosaminoglycans was performed by treatment of $2 \times 10^5$ cells with a mixture of heparinase II (25 units/ml, Sigma, St. Louis, Mo.) and chondroitinase ABC (5 units/ml, Sigma) in 500 µl of HBSS buffer for 1 hour at 37° C. Alternatively, the above preparation was treated with 500 µg pronase (EMD Biosciences, San Diego, Calif.) for 45 minutes at 37° C. Removal of sialic acid was performed by incubating cells with 50 mU/ml neuraminidase from *Vibrio cholerae* (Sigma) at 37° C. for 1 hour. These data indicate that P-Selectin ligands on the surface of 4T1 cells are sulfated proteoglycans, most likely the glycosaminoglycans heparan sulfate or chondroitin sulfate.

Example 8

Figure 8:
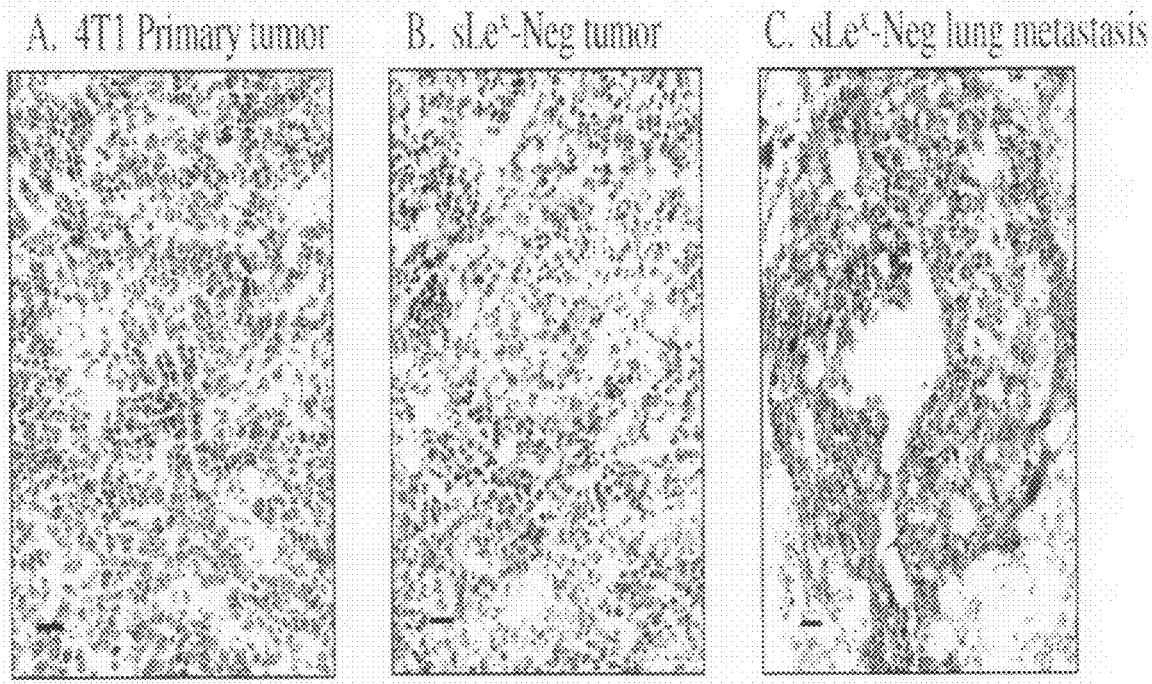
FIG. 8 illustrates histochemical binding of P-Selectin to the primary mass and metastatic pulmonary tumors. P-Selectin ligands were expressed uniformly and strongly on cells of the primary mass in both parental 4T1 cells (FIG. 8A) and sialyl-Lewis X Negative cells (sLe$^x$-Neg) (FIG. 8B). P-Selectin ligands were very strongly expressed on metastatic cells in lung sections (FIG. 8C). Bar equals 20 μm.

P-Selectin ligands are stably expressed on the surface of 4T1 cells. To examine the stability of expression in vivo, pathological samples from primary 4T1 and 4T1 $sLe^x$-Neg variant tumors were stained (FIG. 8). P-Selectin histochemistry was performed as follows: primary tumors and lungs were harvested from mice inoculated with the 4T1 cells at 21 days post inoculation, placed in optimal cutting temperature compound (Ted Pella Inc., Redding, Calif.) and frozen in liquid nitrogen. Five micron frozen sections were fixed for 10 minutes in cold acetone and then washed with cold DPBS (Cellgro® Mediatech, Herndon, Va.). Endogenous peroxidase was blocked by immersion in 0.3% (w/v) hydrogen peroxide in absolute methanol for 15 minutes followed by DPBS wash. Non-specific binding was blocked by incubating with DPBS+1% BSA at room temperature for 20 minutes. Sections were then incubated with recombinant mouse P-Selectin/human FC chimera (R&D systems, Minneapolis, Minn.) for 30 minutes in DPBS+0.2% BSA at room temperature and then washed in DPBS. Sections were incubated with anti-human IgG (Fc specific) peroxidase conjugate (1/300 dilution) for 15 minutes at room temperature followed by DPBS wash. Sections were incubated with diaminobenzidine solution (DAB) for 5 minutes at room temperature, washed with distilled water, counterstained with methyl green, mounted, and examined under a light microscope. Primary antibody was omitted in negative controls to rule out non-specific binding of the secondary antibody. P-Selectin ligands were observed to be significantly and stably expressed on the surface of tumor cells in the primary and secondary lesions, and expression was similar for both 4T1 and $sLe^{x/a}$-Neg variant tumors. Therefore, P-Selectin ligands play a role in hematogenous metastasis in this syngeneic breast cancer model.

Example 9

Figure 9:
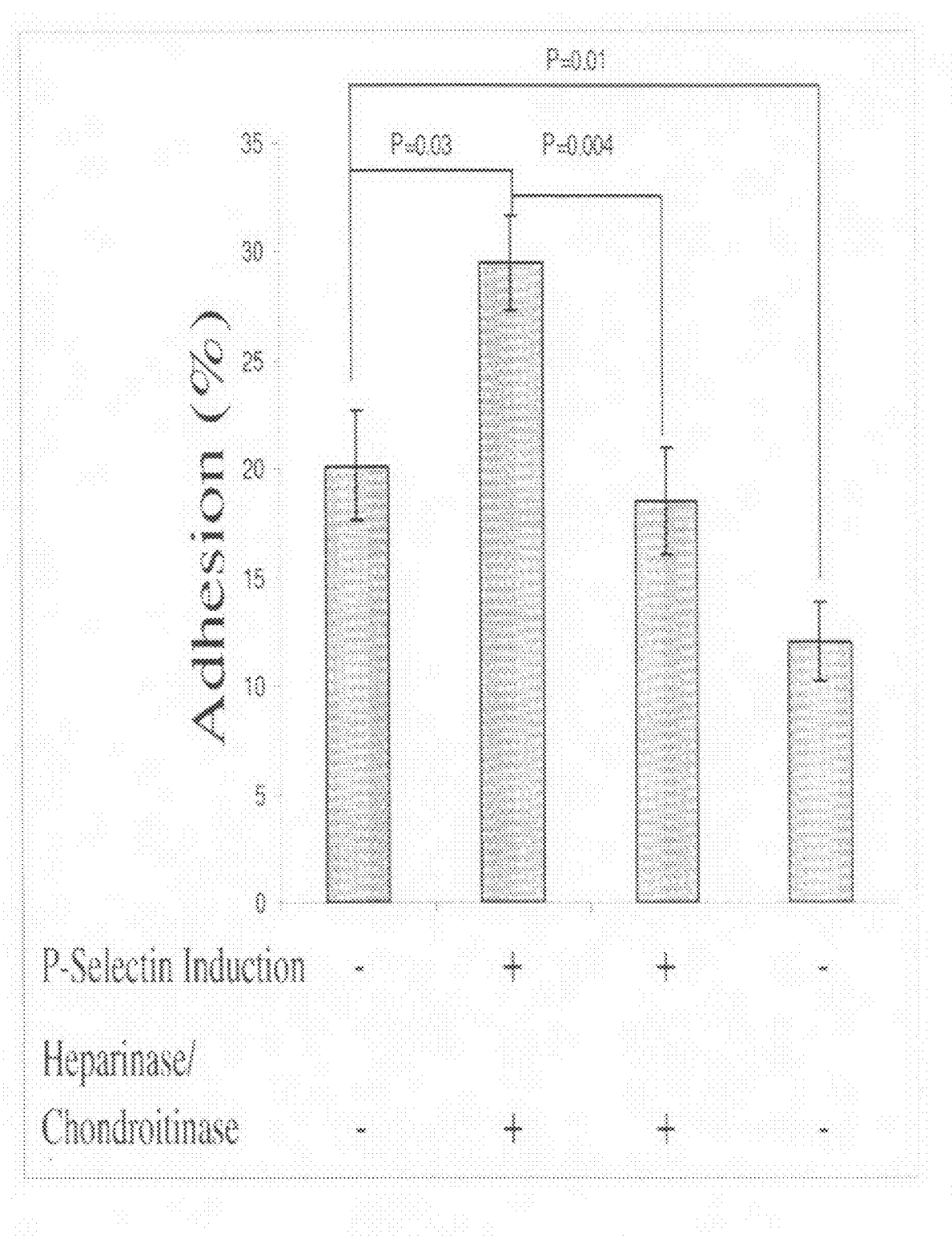
FIG. 9 illustrates involvement of P-Selectin ligands in binding to human vascular endothelial cells. Percentage of adhesion was calculated based on mean fluorescence intensities and presented as average of 11 replications. Bars represent SD based on 11 replications. A representative experiment out of three is shown. Paired Student's t test was used to compare the means.

Interaction of P-Selectin and its ligands play an important role in 4T1 cells binding to HUVECs (FIG. 9). To measure tumor cell adhesion to endothelial cells, Clonetics™ human umbilical vein endothelial cell (HUVEC) system was used (Cambrex Biosciences, Walkersville, Md.). A monolayer of HUVEC cells was prepared. HUVECs were incubated with supplied medium supplemented with IL-4 (20 ng/ml) for 24 hours. Medium was replaced with similar medium supplemented with Prostaglandin E2 (PGE2) for 10 minutes. Calcein AM-labeled (Molecular Probes, Eugene, Oreg.) 4T1 cells were treated with chondroitinase/heparinase, then added to the activated monolayers of HUVECs. Cells were co-incubated at 37° C. for 30 minutes and then unbound 4T1 cells were removed by washing gently with pre-warmed medium. PBS was added to all wells and fluorescence measured and percentage of adhesion was calculated. Stimulating surface expression of P-Selectin on HUVECs led to an increase in adhesion to the 4T1 cells. The adhesion to 4T1 cells was significantly inhibited by treatment with the mixture of heparinase and chondroitinase. There was background adhesion to HUVECs, which was also significantly inhibited by treating the 4T1 cells with heparinase/chondroitinase mix, implying a constitutive presence of P-Selectin on the HUVECs under our experimental conditions. This was confirmed by examining P-Selectin expression on HUVECs. A low constitutive expression of P-Selectin was detected on 10% of cells, which was elevated to a more intense staining on about 20% of cells after treatment with IL-4 and PGE2. Adhesion was clearly enhanced after P-Selectin induction on HUVECs and suppressed after heparinase/chondroitinase treatment of tumor cells (FIG. 9).

Example 10

Heparin inhibits both P-Selectin binding to the tumor cells and tumor cell-platelet interactions mediated by P-Selectin.

Figure 10:
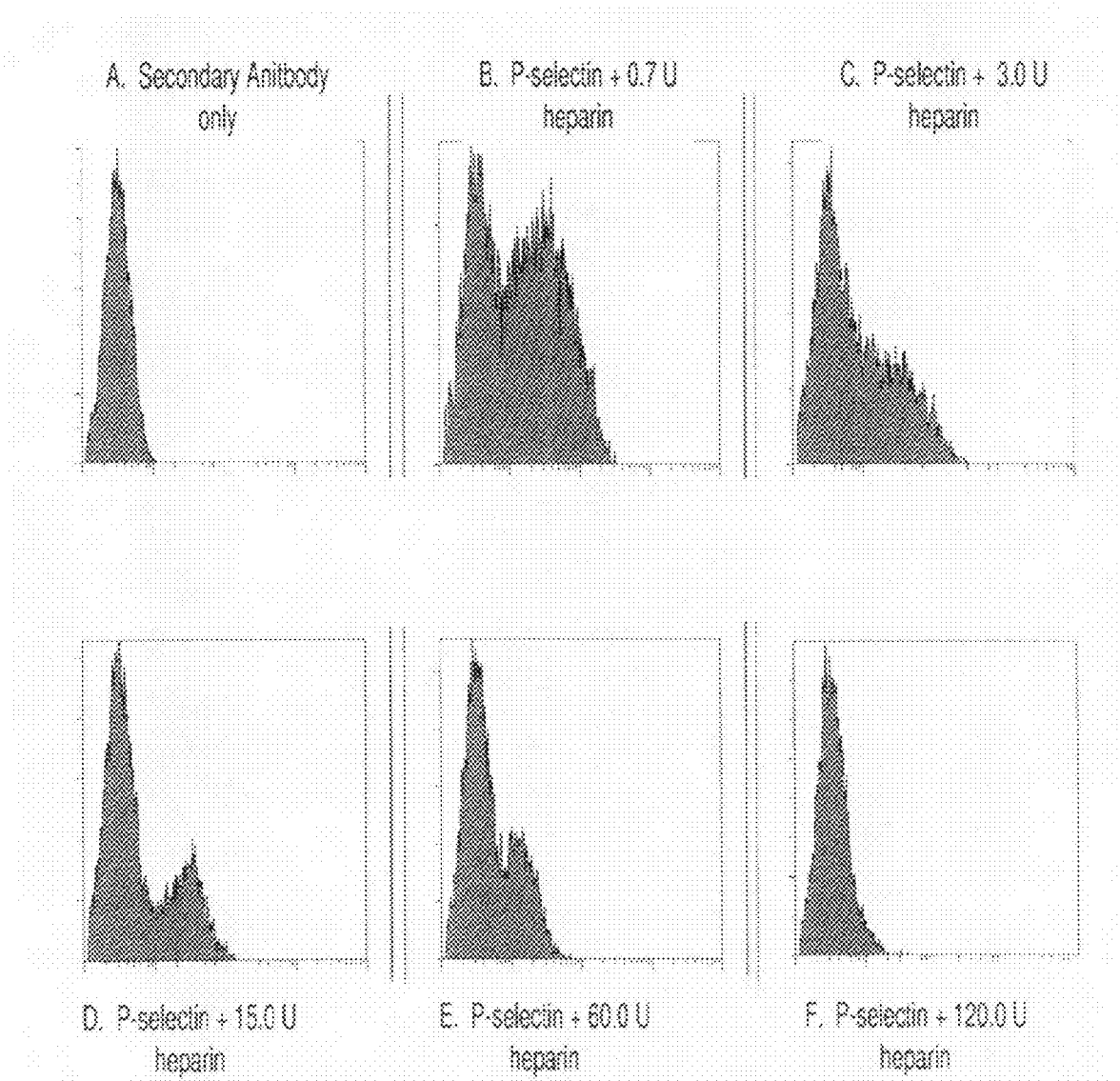
FIG. 10 illustrates the effect of heparin on P-Selectin interaction with sLe$^x$-Neg tumor cells.

Heparin's ability to inhibit P-Selectin interaction with the cell surface in vitro was tested using the sLe$^x$-Neg 4T1 cell variant. Recombinant P-Selectin was incubated with heparin and then the mixture was added to cells to test the binding (FIG. 10). Heparin efficiently inhibited P-Selectin binding to cells in a dose dependent manner.

Example 11

Figure 11:
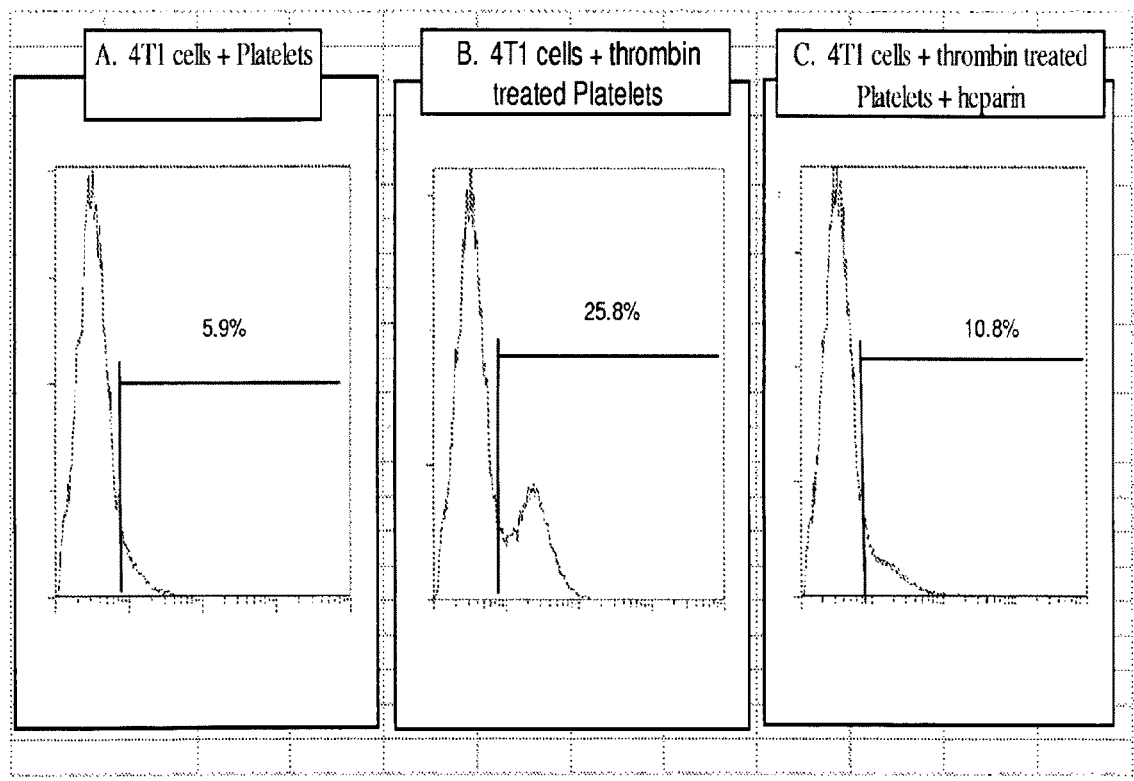
FIG. 11 illustrates that heparin inhibits binding of mouse platelets to 4T1 cells.

To examine if heparin can block the interaction of mouse platelets with tumor cells, 4T1 cells were mixed with Calcein-AM-labeled mouse platelets in the presence of mouse thrombin with or without heparin. Mouse thrombin was added to stimulate relocation of P-Selectin to platelet surface and tumor cells were then analyzed by flow cytometry for Calcein-AM staining, indicating platelet attachment. Thrombin treated platelets showed binding to tumor cells, which was reduced in the presence of heparin (FIG. 11). Blood was collected into sodium citrate (0.38% w/v) from naive mice and platelets were isolated from plasma by centrifugation. Platelet were washed and labeled with 5 µM final Calcein-AM (Molecular Probes, Eugene, Oreg., USA) for 15 minutes at 37° C. Platelets were then washed and incubated with 1 U/ml thrombin (Haematologic Technologies Inc, Essex Junction, Vt.) at 37° C. for 10 minutes. Heparin (Baxter Healthcare Corp., Deerfield, Ill., 100 U/ml final concentration) was then added to the mixture of platelets and thrombin, and incubated with 4T1 cells in flow cytometry tubes, for 15 minutes at room temperature, then acquired and analyzed by flow cytometry.

FIG. 11A illustrates lack of binding of 4T1 cells incubated with untreated platelets. FIG. 11B illustrates binding of 4T1 cells to platelets which had been pre-treated with thrombin. FIG. 11C illustrates that heparin can inhibit binding of 4T1 cells to platelets which had been pre-treated with thrombin. The data illustrate that tumor cell-platelet interaction is P-Selectin mediated and can be blocked by heparin.

Example 12

It has been shown that heparin administration at clinically relevant dose inhibited lung metastasis in experimental models, where tumor cells were delivered directly into the blood stream (8). However, in order to translate the results into clinical practice, such experimental evaluations should be performed in syngeneic spontaneous models. The murine mammary 4T1 cell line is a perfect model. In particular, sLe$^x$-Neg variant is an appropriate model as it does not express overlapping selectin reactive epitopes sLe$^{x/a}$.

BALB/c female mice (6-8 weeks old) were purchased from Harlan (Indianapolis, Ind.). Tumors were established as described earlier (9). Briefly, each mouse was inoculated subcutaneously in the abdominal mammary gland with 5×10$^4$ 4T1 cells. To establish a functional correlation between P-Selectin ligand expression of 4T1 cells and their metastatic ability in vivo, we injected mice with 100 units of heparin 30 minutes before tumor cell inoculation. Mice were sacrificed 26 days after tumor inoculation, lungs were harvested and metastatic cells were detected by clonogenic assay. We observed a complete absence of metastases in lung of majority of mice (six mice out of total of seven) injected with heparin (Table 3). All mice that were injected with PBS as control developed lung metastasis. Thus, blocking of P-Selectin interaction with its ligand in vivo significantly prevented establishment of metastatic foci.

TABLE 3

Number of mice detected positive for established lung metastases in groups administered with heparin or PBS. Total number of mice examined in each experiment is given in the parenthesis.

| Treatment | Positive (total) |
|---|---|
| PBS | 6 (6) |
| Heparin | *1 (7) |

*P = 0.0047 as compared with PBS treated group by Fisher exact test.

Similarly, no mice were detected positive for lung metastases after treatment with Chondroitinase ABC (Table 4).

TABLE 4

Number of mice detected positive for established lung metastases after chonditinase ABC treatment of the cancer cells.

| Treatment | Positive (total) |
|---|---|
| ChABC | *0 (5) |
| Non-treated | 5 (5) |

*P = 0.0079 as compared with group injected with non-treated cells by Fisher exact test.

Example 13

Figure 12:
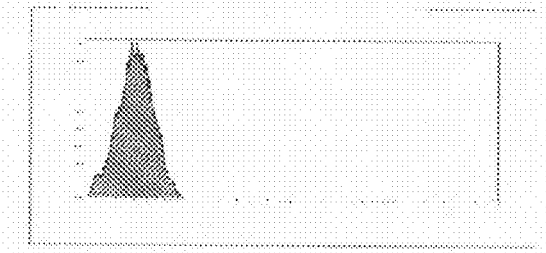
FIG. 12 illustrates that chondroitin sulfates are P-Selectin ligands on 4T1 cells.
Figure 12:
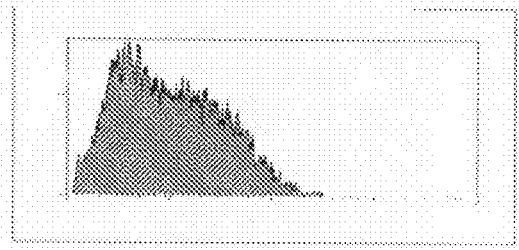
Figure 12:
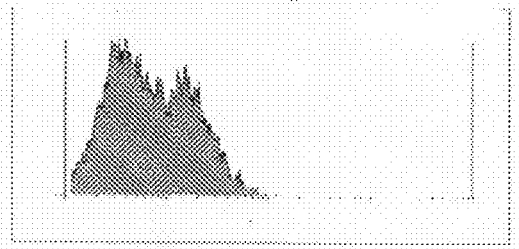
Figure 12:
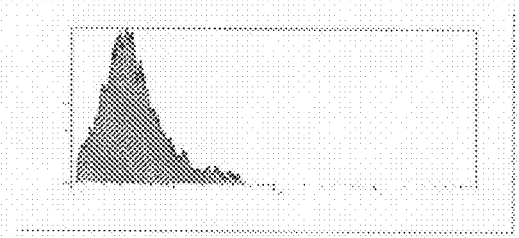
Figure 12:
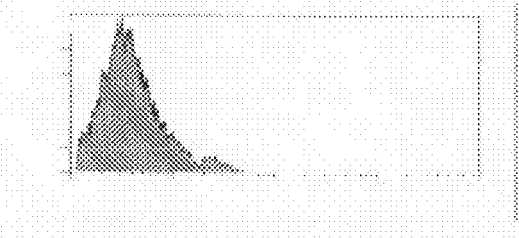

P-Selectin binds to CS PGs on the surface of human renal adenocarcinoma (10). To further explore the nature of P-Selectin ligands on the 4T1 tumor cell line, used heparinase and chondroitinase ABC were used separately in P-Selectin binding assays. The data indicate a major role for CS in P-Selectin binding to the 4T1 cells (FIG. 12). FIG. 12A illustrates 4T1 cells incubated with secondary antibody alone. FIG. 12B illustrates P-Selectin binding to 4T1 cells. FIG. 12C illustrates P-Selectin binding to 4T1 cells which had been pre-treated with heparinase. FIG. 12D illustrates P-Selectin binding to 4T1 cells which had been pre-treated with chondroitinase. FIG. 12E illustrates P-Selectin binding to 4T1 cells which had been pre-treated with both heparinase and chondroitinase.

Example 14

Figures 13A, 13B, 13C, 13D, 13E, 13F:
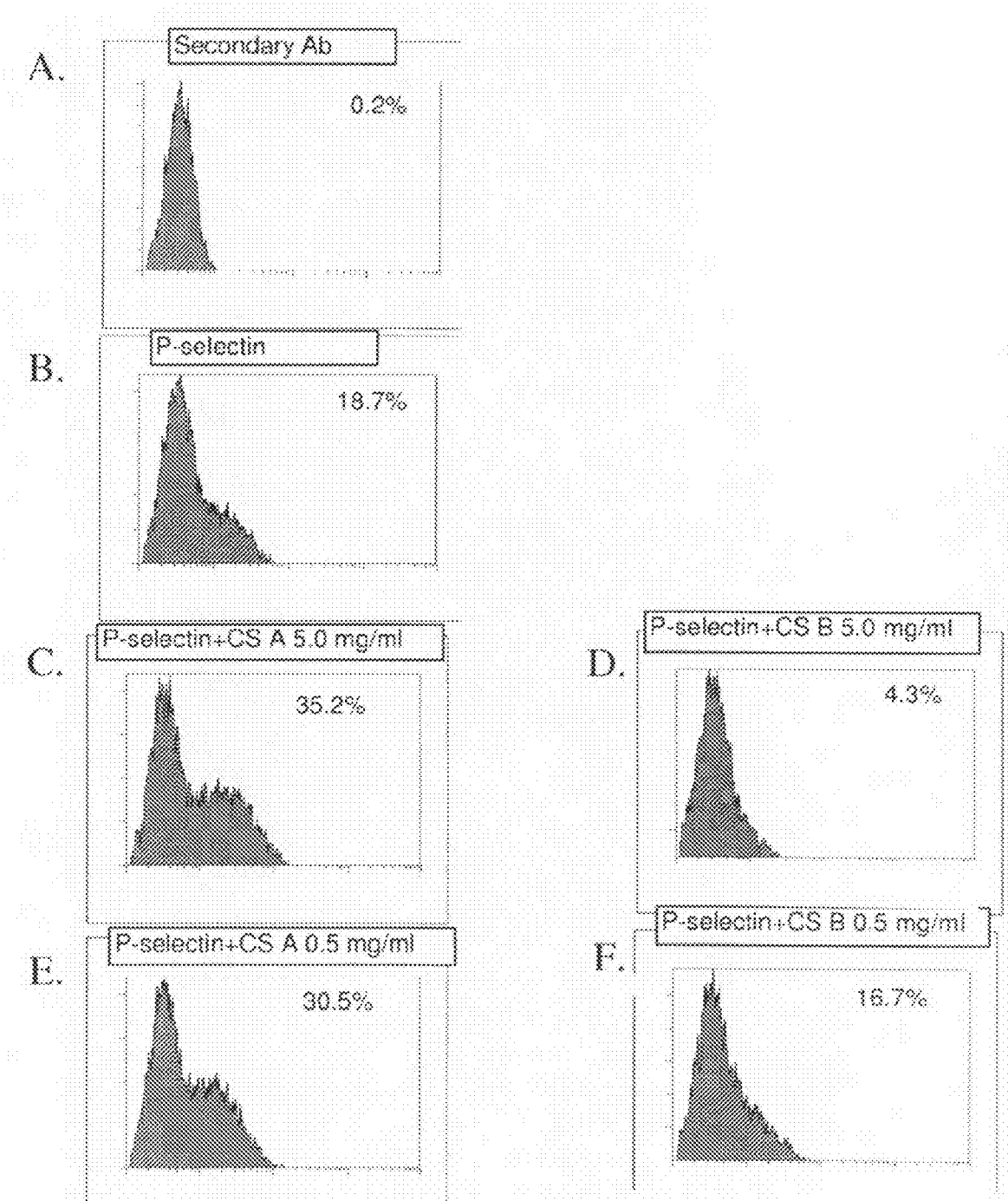
FIG. 13A illustrates 4T1 cells incubated with secondary antibody alone.
FIG. 13B illustrates P-Selectin binding to 4T1 cells.
FIG. 13C illustrates P-Selectin binding to 4T1 cells when the P-Selectin had been pre-treated with 5.0 mg/ml chondroitin sulfate A.
FIG. 13D illustrates P-Selectin binding to 4T1 cells when the P-Selectin had been pre-treated with 5.0 mg/ml chondroitin sulfate B.
FIG. 13E illustrates P-Selectin binding to 4T1 cells when the P-Selectin had been pre-treated with 0.5 mg/ml chondroitin sulfate A.
FIG. 13F illustrates P-Selectin binding to 4T1 cells when the P-Selectin had been pre-treated with 0.5 mg/ml chondroitin sulfate B.
Figures 13G, 13H, 13I, 13J:
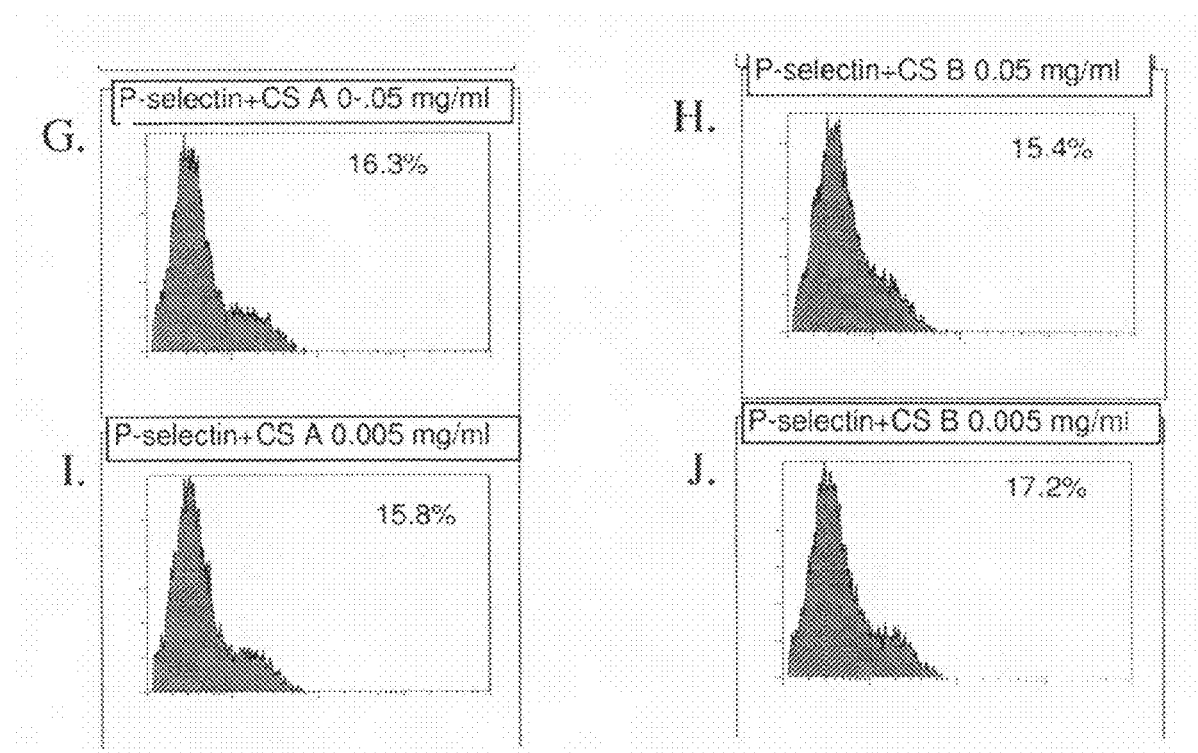
FIG. 13G illustrates P-Selectin binding to 4T1 cells when the P-Selectin had been pre-treated with 0.05 mg/ml chondroitin sulfate A.
FIG. 13H illustrates P-Selectin binding to 4T1 cells when the P-Selectin had been pre-treated with 0.05 mg/ml chondroitin sulfate B.
FIG. 13I illustrates P-Selectin binding to 4T1 cells when the P-Selectin had been pre-treated with 0.005 mg/ml chondroitin sulfate A.
FIG. 13J illustrates P-Selectin binding to 4T1 cells when the P-Selectin had been pre-treated with 0.005 mg/ml chondroitin sulfate B.
Figure 14:
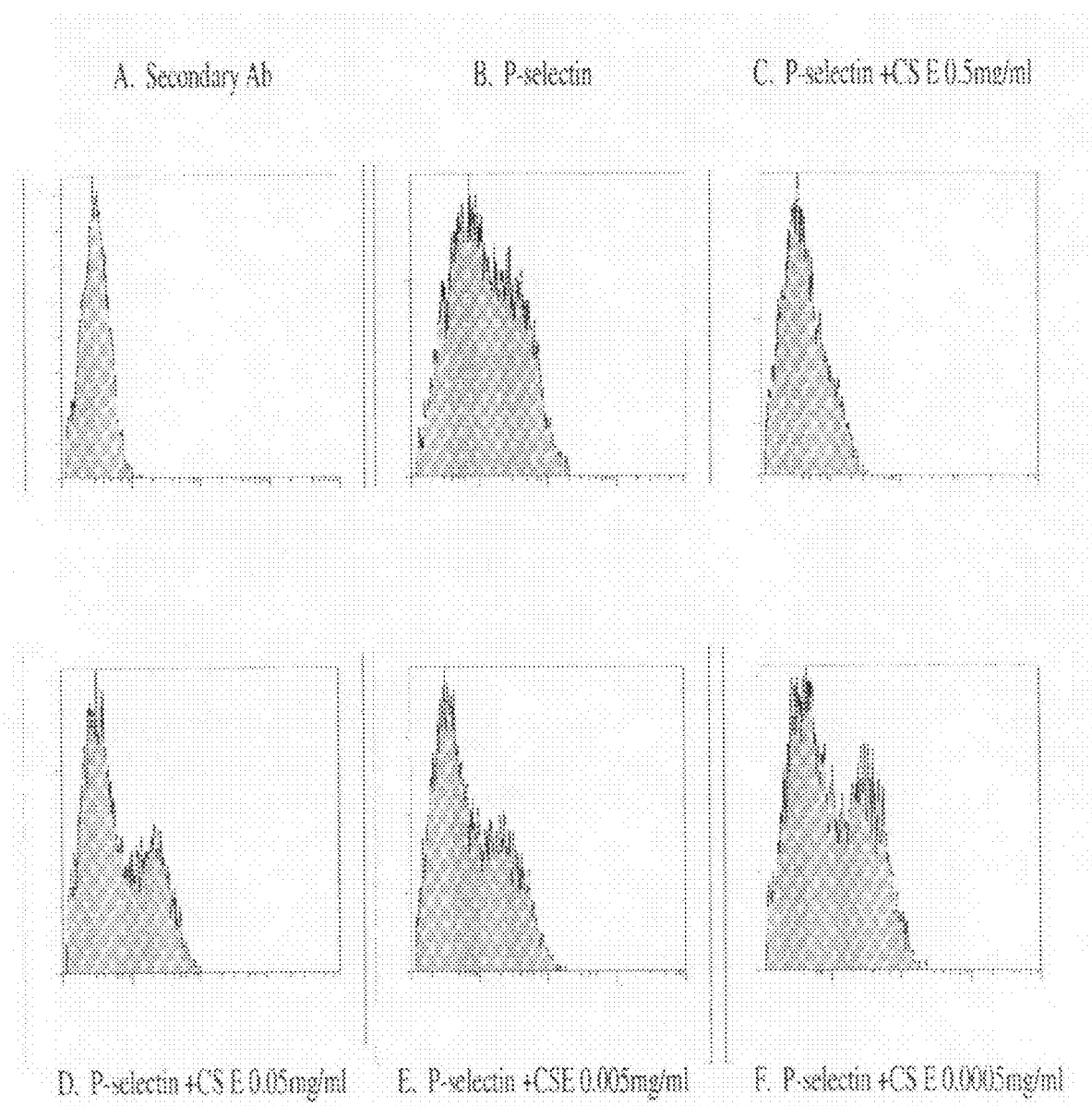
FIG. 14 illustrates inhibition of P-Selectin binding to 4T1 cells by chondroitin sulfate.

Chondroitin sulfates, including chondroitin sulfates A, B, C and E, block the interaction of P-Selectin to cancer cells. Binding of recombinant P-Selectin to cells was examined after treatment with heparinase and chondroitinase ABC or in the presence of various concentrations of heparin and chondroitin sulfate A, B, C, and E (Seikagaku America, Falmouth, Mass.). Among those tested, CS B (dermatan sulfate) and CS E inhibited P-Selectin binding to the cells (FIGS. 13 and 14). CS A and C (data not shown) showed minimal inhibitory effects. CS B showed inhibitory effects only at higher concentrations, while CS E was a more potent inhibitor with a complete inhibition at a concentration of 0.5 mg/ml. The effective dose of heparin, 120 units (FIG. 10), corresponds to 0.7 mg/ml heparin, which is close to the CS E blocking concentration of 0.5 mg/ml. FIG. 13A illustrates 4T1 cells incubated with secondary antibody alone. FIG. 13B illustrates P-Selectin binding to 4T1 cells. FIG. 13C illustrates P-Selectin binding to 4T1 cells when the P-Selectin had been pre-treated with 5.0 mg/ml chondroitin sulfate A. FIG. 13D illustrates P-Selectin binding to 4T1 cells when the P-Selectin had been pre-treated with 5.0 mg/ml chondroitin sulfate B. FIG. 13E illustrates P-Selectin binding to 4T1 cells when the P-Selectin had been pre-treated with 0.5 mg/ml chondroitin sulfate A. FIG. 13F illustrates P-Selectin binding to 4T1 cells when the P-Selectin had been pre-treated with 0.5 mg/ml chondroitin sulfate B. FIG. 13G illustrates P-Selectin binding to 4T1 cells when the P-Selectin had been pre-treated with 0.05 mg/ml chondroitin sulfate A. FIG. 13H illustrates P-Selectin binding to 4T1 cells when the P-Selectin had been pre-treated with 0.05 mg/ml chondroitin sulfate B. FIG. 13I illustrates P-Selectin binding to 4T1 cells when the P-Selectin had been pre-treated with 0.005 mg/ml chondroitin sulfate A. FIG. 13J illustrates P-Selectin binding to 4T1 cells when the P-Selectin had been pre-treated with 0.005 mg/ml chondroitin sulfate B.

Example 15

FIG. 14A illustrates 4T1 cells incubated with secondary antibody alone. FIG. 14B illustrates P-Selectin binding to 4T1 cells. FIG. 14C illustrates P-Selectin binding to 4T1 cells when the P-Selectin had been pre-treated with 0.5 mg/ml chondroitin sulfate E. FIG. 14D illustrates P-Selectin binding to 4T1 cells when the P-Selectin had been pre-treated with 0.05 mg/ml chondroitin sulfate E. FIG. 14E illustrates P-Selectin binding to 4T1 cells when the P-Selectin had been pre-treated with 0.005 mg/ml chondroitin sulfate E. FIG. 14F illustrates P-Selectin binding to 4T1 cells when the P-Selectin had been pre-treated with 0.0005 mg/ml chondroitin sulfate E. These data indicate that chondroitin sulfate is the major P-Selectin ligand on the surface of the 4T1 cells. Oversulfated CS E is able to effectively inhibit the interactions.

Example 16

Figure 15:
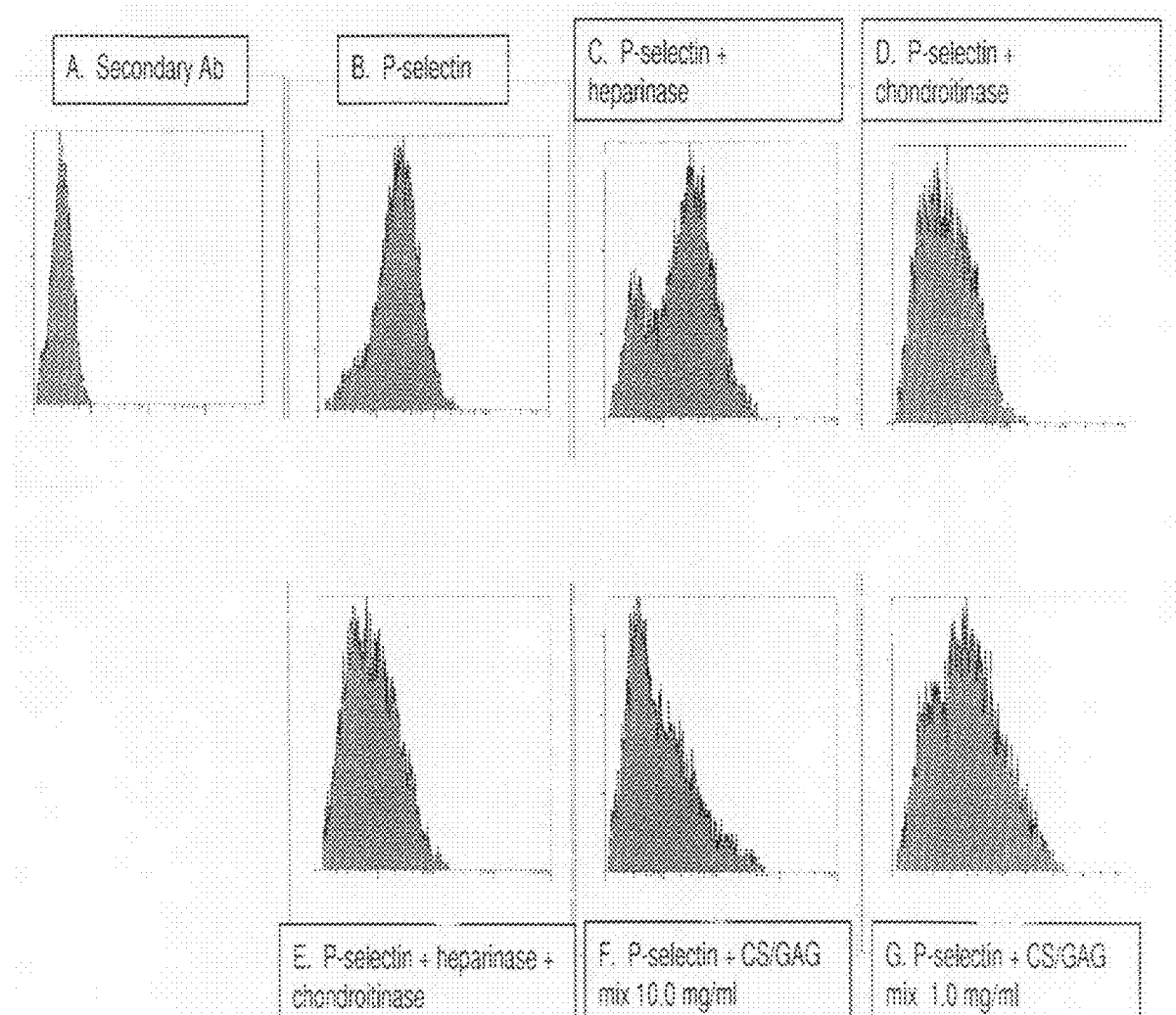
FIG. 15 illustrates that CS PGs are the main P-Selectin ligands on the surface of a human breast cancer cell line. Inhibition of P-Selectin binding to metastatic human breast cancer cells chondroitinase or a mixture of glycosaminoglycans and chondroitin sulfate is illustrated.

The bone-colonizing human breast cancer cell variant MDA-MET was tested for expression of P-Selectin ligands. P-Selectin reactivity with cells was decreased after chondroitinase treatment (FIG. 15). Heparinase or a mixture of heparinase and chondroitinase did not affect P-Selectin binding. This data suggests that CS PGs can also be a major P-Selectin ligand on the surface of human breast cancer cells. FIG. 15A illustrates MDA-MET cells incubated with secondary antibody alone. FIG. 15B illustrates P-Selectin binding to MDA-MET cells. FIG. 15C illustrates P-Selectin binding to MDA-MET cells when the cells had been pre-treated with heparinase. FIG. 15D illustrates P-Selectin binding to MDA-MET cells when the cells had been pre-treated with chondroitinase. FIG. 15E illustrates P-Selectin binding to MDA-MET cells when the cells had been pre-treated with both heparinase and chondroitinase. FIG. 15F illustrates P-Selectin binding to MDA-MET cells when the P-Selectin had been pre-treated with 10.0 mg/ml of a chondroitin sulfate and glycosaminoglycan mixture. FIG. 15G illustrates P-Selectin binding to MDA-MET cells when the P-Selectin had been pre-treated with 1.0 mg/ml of a chondroitin sulfate and glycosaminoglycan mixture.

Example 17

Real-time PCR was conducted to quantify mRNAs of five genes in four different human breast cancer tumor lines. The assayed genes were Syndecan-1 (SDC-1), Neuropilin-1 (NRP-1), Syndecan-4 (SDC-4), MCSP, and estrogen receptor 1. The tumor lines were MCF-7, MDA-MD-468 (MDA-468), MDA-MB-231 (MDA-231), and MDA-MET. MCF-7 and MDA-468 are less aggressive. MDA-231 is an aggressive cell line, and MDA-MET is a subline of MDA-231 that metastasizes to bone. The quantity of each mRNA was assayed in comparison to 18s RNA. The results are shown in Table 5. NRP-1, SDC-4 and MCSP expression was higher in the two more aggressive cell lines than in either of the two less aggressive cell lines. The results suggest a down regulation of SDC-1 and an up regulation of SDC-4 is related to the more aggressive phenotype. MCF-7 and MDA-468 are epithelial-like, while both MDA-231 and MDA-MET cells are mesenchymal type. Thus, high expression of NRP-1, MCSP and SDC-4 may be related to an epithelial to mesenchymal transition, which is a phenotypic event associated with more metastasis and aggressive growth.

TABLE 5

| | Ratio of mRNA for indicated genes to 18s RNA. | | | |
|---|---|---|---|---|
| Antigen | MCF7 | MDA-468 | MDA-231 | MDA-MET |
| SDC-1 | 0.37 | 2.3 | 0.26 | 0.17 |
| NRP-1 | 0.84 | 0.91 | 1.32 | 1.99 |
| SDC-4 | 0.67 | 0.83 | 1.2 | 2.01 |
| MCSP | 0.01 | 0.02 | 3.14 | 1.53 |
| Estrogen receptor 1 | 5.13 | 0.13 | 0.15 | 0.11 |

Example 18

Figure 16:
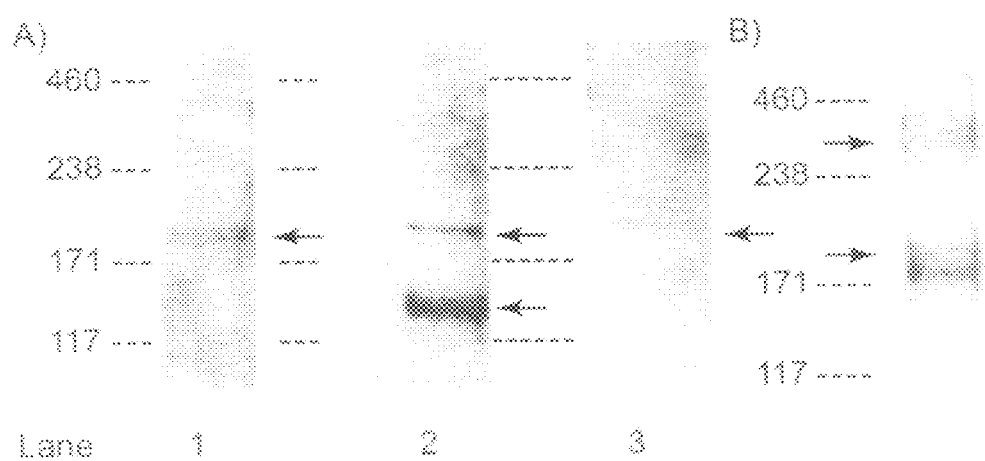
FIG. 16. Western Blot. A) MDA-MB231 cell lysate subjected to SDS-PAGE and the gel probed with recombinant human P-Selectin (lane 1), anti-NRP-1 (C-19 antibody, lane 2), and anti-chondroitin sulfate-A (2H6 antibody, lane 3). B) Immunoprecipitated fraction of cleared MDA-231 lysate immunoprecipitated with P-Selectin on protein G beads (DYNA BEADS system), probed with anti-NRP-1.

Cell lysates of MDA-231 tumor cells were probed by Western blotting to identify NRP-1 protein and the proteins that bind P-Selectin. The results are shown in FIG. 16. In FIG. 16, panel A, lane 1, an MDA-231 cell lysate is probed with recombinant P-Selectin, and in lane 2 with anti-Neuropilin-1, and in lane 3 with anti-CS-A. The long arrow indicates the NRP-1 core protein. The short arrows indicate NRP-1 with a sulfated glycosaminoglycan (GAG) chain. Panel B shows a Western blot of proteins that were immunoprecipitated by P-Selectin (attached to Protein G beads (DYNA BEADS system)). The gel in panel B was probed with anti-NRP-1. These data indicate that Neuropilin-1 is decorated with CS and is one of the primary proteins of MDA-231 cell lysate that is bound by P-Selectin, and that only the CS-decorated form of Neuropilin-1 binds to P-Selectin.

Example 19

Figure 17:
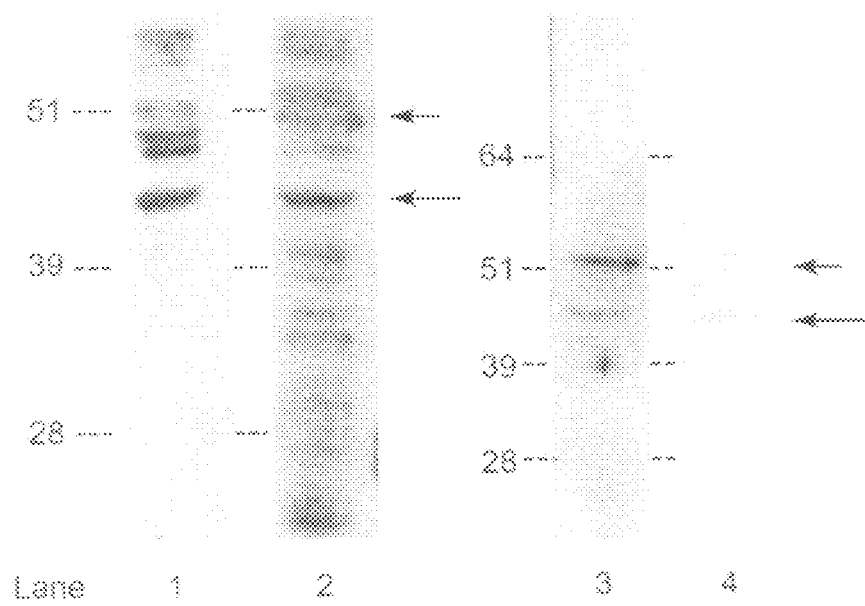
FIG. 17. Western blot. MDA-231 cell lysate was probed with polyclonal anti-Syndecan-4 (lanes 1, 3, and 4) and recombinant human P-Selectin (lane 2). Lanes 1, 2, and 4 are total cell lysate. Lane 3 is the immunoprecipitated fraction of cleared MDA-231 cell lysate immunoprecipitated with P-Selectin on protein G beads (DYNA BEADS system).

Analogously to Example 18, MDA-231 cell lysate was analyzed by Western blotting with anti-Syndecan-4 and human P-Selectin. The results are shown in FIG. 17. Lanes 1, 2, and 4 are total cell lysates of MDA-231. Lane 3 is proteins immunoprecipitated with P-Selectin, as in Example 18. Lanes 1, 3, and 4 were probed with polyclonal anti-Syndecan-4 antibodies. Lane 2 is probed with P-Selectin. Arrows show bands that correspond to Syndecan-4 and react with P-Selectin. These data show that Syndecan-4 binds to P-Selectin.

Example 20

Figure 18:
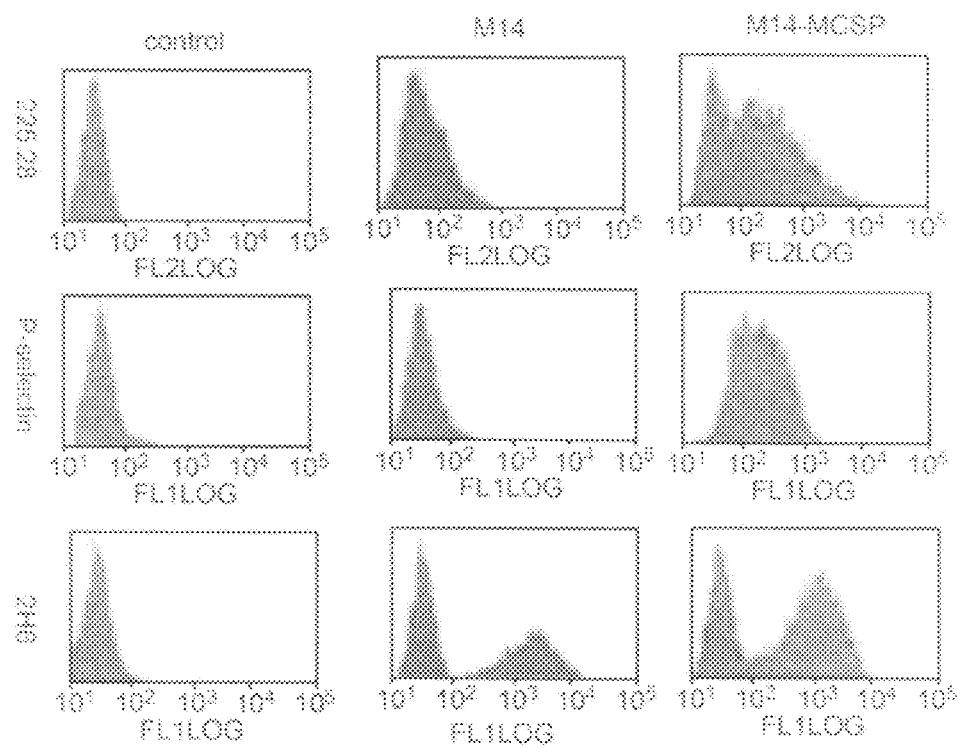
FIG. 18. FACS analysis of M14 melanoma cells, or M14 cells transfected with a vector expressing MCSP (M14-MCSP). Cells were analyzed with an anti-CS-A antibody (2H6), anti-MCSP (225.28), or P-Selectin. The control panels were M14 cells labeled only with secondary antibody.

The melanoma cell line M14 does not express MCSP. M14 and M14 cells transfected with a vector to express MCSP were analyzed by fluorescence activated cell sorting (FACS) with antibodies against CS-A (225.28), antibodies against MCSP (2H6) and P-Selectin coupled to human Fc chain in FIG. 18. The cells labeled with primary antibody or P-Selectin were then reacted with secondary fluorescently labeled anti-Fc antibody and sorted. The leftmost panels of FIG. 18 are control M14 cells labeled only with secondary antibody. The middle panels labeled M14 are untransformed M14 cells labeled with the primary antibody or P-Selectin shown on the left. The right most panels are M14-MCSP cells. The results suggest that binding of P-Selectin to the tumor cells is via MCSP.

Example 21

Figure 19:
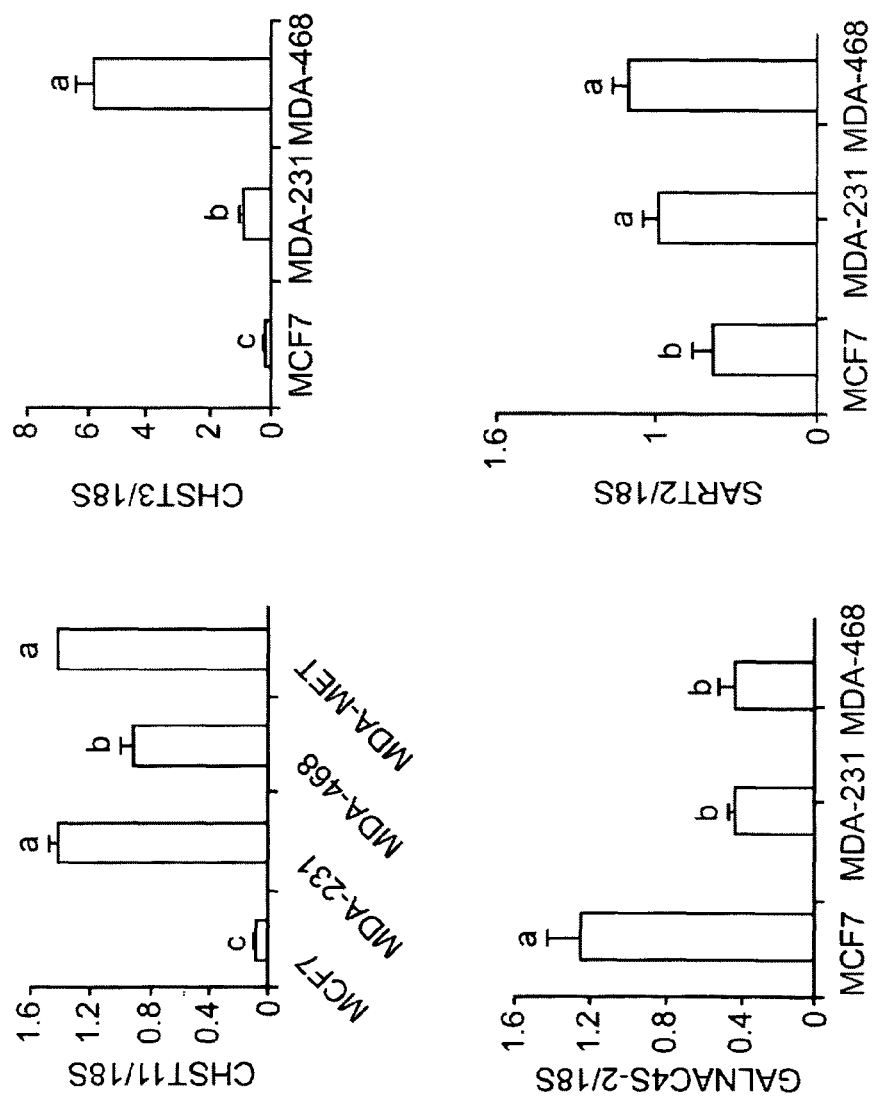
FIG. 19. Relative expression of four genes involved in chondroitin sulfate biosynthesis in the cell lines MCF7, MDA-231, MDA-468, and MDA-MET. The ratio of the mRNA as assayed by real-time PCR is shown as a ratio to 18S RNA. The raw data were log transformed and subtracted by 18S RNA levels for statistical analysis. Comparisons were made by ANOVA and post-hoc analysis and significant differences are shown by letters.

As in Example 17, real-time PCR was used to quantify mRNA of several enzymes involved in CS biosynthesis. The results are shown in FIG. 19. The tested mRNAs were for C4ST-1 (also known as CHST11), which synthesizes CS-A, GalNAc4S-6ST, which synthesizes CS-E, CHST3, which synthesizes CS-C, and SART2, which is dermatin sulfate epimerase and converts CS-A to CS-B. The data show CHST11 mRNA is highest in MDA-231 and MDA-MET cells, the more aggressive of the four tumor cell lines tested, and lower in the less aggressive lines MCF7 and MDA-468. The other genes assayed were also highly expressed in most or all of the tumor lines, but were not more highly expressed in the two aggressive tumor lines than in the two less aggressive tumor lines.

Example 22

In this experiment, gene expression levels were assayed by real-time PCR and comparison to 18S RNA levels. The dependence of gene expression on methylation levels was tested by treating tumor cells with varying levels of 5-aza-2'-deoxycytidine (5azadC), which is a demethylating agent (Table 6). Methylation of CpG islands is a well-known mechanism of gene control. Methylation decreases expression of genes whose promoters are methylated. The expression of NRP-1, CHST11, and MCPG each increased with increasing 5azadC concentration, which indicates they are under methylation control, with increased methylation repressing expression of the genes. Urokinase (uPA) was used as a positive control. Syndecan-4 expression decreased or remained approximately constant with 5azadC treatment, indicating it is not under methylation control.

TABLE 6

Expression of indicated genes in MCF-7 cells after treatment with 5azadC. Relative expression levels are shown compared with no (0 μm) 5azadC.

| 5azadC (μM) | NRP-1 | CHST11 | MCPG | uPA | Synd-4 |
|---|---|---|---|---|---|
| 0 | 1 | 1 | 1 | 1 | 1 |
| 0.5 | 1.04 | 1.34 | 1.3 | 2.2 | 0.7 |
| 1 | 1.50 | 1.68 | 1.4 | 2.9 | 0.5 |
| 5 | 1.72 | 3.7 | 1.7 | 3.2 | 0.8 |
| 20 | 1.71 | 4.00 | 2.1 | 3.9 | 0.6 |

Example 23

Figure 20:
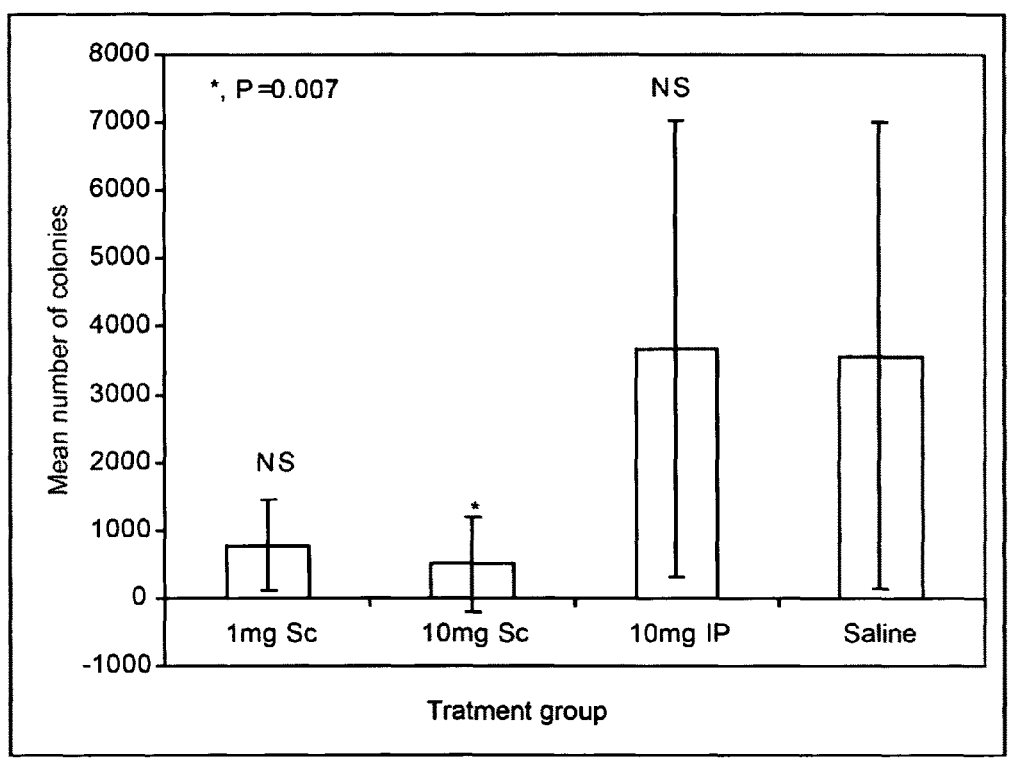
FIG. 20. Chondroitin sulfate inhibits metastasis. Mice were injected with 4T1 cells into fact pads. After tumors were palpable (3-4 days after transplant) they were daily injected with CS intraperitoneally (ip) or subcutaneously (sc). Micer were sacrificed 30 days after transplant and lung colonies were quantified. Saline injection was used as a control. Comparisons were made between groups treated with CS and the saline group as control. NS, not significant. Average and SD with three animals per group is shown.

This Example demonstrates that administration of CS reduces metastasis. Mice were injected with 4T1 cells into fat pads. After tumors were palpable (3-4 days after transplant) the mice were daily injected with CS intraperitoneally (ip) or subcutaneously (sc). The mice were sacrificed 30 days after transplant and lung colonies were quantified. CS was dissolved in saline for injection. Saline control injection by either sc or ip routes produced similar results. Injection of either 1 mg or 10 mg CS subcutaneously decreased metastasis compared to saline control, but injection intraperitoneally did not appear to (FIG. 20).

Characterization of P- and E-Selectin ligands is important for the assessment of metastatic risk and the development of possible ways of dealing with metastatic disease. A significant amount of P-Selectin binding is both $Ca^{2+}$-independent and sialic acid-independent, confirming that $sLe^x$ is not a P-Selectin ligand on 4T1 cells.

While $sLe^{x/a}$ oligosaccharides are common ligands for both E- and P-Selectin, these two lectins do not correlate in their reactivity with the 4T1 cells. P-Selectin binds to the 4T1 cells strongly and the binding is not affected by sorting for $sLe^x$ oligosaccharide by KM93 antibody or even by FTIII gene transfection. E-Selectin binding can be predicted by reactivity of anti-$sLe^x$ antibodies, indicating that E-Selectin binding is predominately $sLe^x$ dependent. However, P-Selectin binding did not correlate with either E-Selectin or $sLe^x$-reactive antibodies, suggesting that much of the P-Selectin binding is not to $sLe^x$ or other related oligosaccharides. There is a correlation between $sLe^x$ reactive antibody binding and E-Selectin binding to tumor cells but no such correlation to P-Selectin binding. The P-Selectin binding in 4T1 is dependent upon structures other than $sLe^x$ or $sLe^a$ ligands with increased $sLe^x$ expression having almost no effect on P-Selectin binding.

E-Selectin binding to the 4T1 cell line is restricted to $sLe^x$ or closely related structures while P-Selectin binding can involve a varied group of compounds, including $Ca^{2+}$-independent binding to non-Lewis structures. Characterization of P-Selectin binding to the 4T1 cells illustrates that this interaction is sulfur dependent and heparinase/chondroitinase sensitive. Further characterization of the 4T1 surface ligands clearly indicate that CS and CS glycosaminoglycans are the major P-Selectin ligands expressed on this cell line. CS B and CS E are able to inhibit the interaction.

The stable expression of P-Selectin ligands on 4T1 cells in vivo suggests that these ligands contribute to the metastatic behavior of this cell line. Cell surface P-Selectin ligands indeed contribute to binding of the 4T1 cells to platelets and HUVECs. Intact P-Selectin reactivity with heparan sulfate or CS may facilitate microemboli formation and adhesion to the endothelial cells, promoting tumor cell arrest in vasculature and extravasation.

Heparin is being used as anticoagulant treatment of venous thromboembolism in cancer patients, where it has been shown to improve patient survival by mechanisms not explained by anticoagulation (11). The present invention clearly demonstrates that Heparin inhibited P-Selectin binding to the 4T1 cells, and it blocked P-Selectin mediated adhesion of platelets to this tumor cell line. This data warranted in vivo testing of heparin for inhibition of metastasis in tumor bearing animals.

Inhibition of interaction between P-Selectin with its various ligands on tumor cells has an anti-metastatic therapeutic effect. Competition studies demonstrate that heparin and CS interaction may involve a region of the P-Selectin molecule very close to the lectin binding site for $sLe^x$. Heparin is capable of blocking P-Selectin binding to various tumor cells with various surface ligands, including $sLe^x$ (12), sulfated glycolipids (13), heparan sulfate PGs (14, 15) and even CS PGs (10). In addition, the binding of a CS proteoglycan to P-Selectin was inhibited by $sLe^x$, which is in agreement with the notion that CS binding to the lectin domain of P-Selectin is similar to $sLe^x$ binding (10). The present data suggest that highly sulfated CS types may be used to block P-Selectin binding to any of its ligands on tumor cells. Such broad specificity can be explained by recognition of a clustered epitope by P-Selectin (6). Targeting P-Selectin interaction with these ligands can be used for treatment of metastatic cancer. The current data support administration of CS as an alternative to treat metastatic disease.

As various changes could be made in the above methods and compositions without departing from the scope of the invention, it is intended that all matter contained in the above description be interpreted as illustrative and not in a limiting sense. Unless explicitly stated to recite activities that have been done (i.e., using the past tense), illustrations and examples are not intended to be a representation that given embodiments of this invention have, or have not, been performed.

As various changes could be made in the above methods and compositions without departing from the scope of the invention, it is intended that all matter contained in the above description be interpreted as illustrative and not in a limiting sense. Unless explicitly stated to recite activities that have been done (i.e., using the past tense), illustrations and examples are not intended to be a representation that given embodiments of this invention have, or have not, been performed.

REFERENCES

1. Fukushi, Y., Nudelman, E., Levery, S. B., Hakomori, S., and Rauvala, H. Novel fucolipids accumulating in human adenocarcinoma. III. A hybridoma antibody (FH6) defining a human cancer-associated difucoganglioside (VI3NeuAcV3III3Fuc2nLc6). J Biol Chem, 259: 10511-10517, 1984.
2. Fukushima, K., Hirota, M., Terasaki, P. I., Wakisaka, A., Togashi, H., Chia, D., Suyama, N., Fukushi, Y., Nudelman, E., and Hakomori, S. Characterization of sialosylated Lewisx as a new tumor-associated antigen. Cancer Res, 44: 5279-5285, 1984.
3. Hanai, N., Shitara, K., and Yoshida, H. Generation of monoclonal antibodies against human lung squamous cell carcinoma and adenocarcinoma using mice rendered tolerant to normal human lung. Cancer Res, 46: 4438-4443, 1986.
4. Hoff, S. D., Matsushita, Y., Ota, D. M., Cleary, K. R., Yamori, T., Hakomori, S., and Irimura, T. Increased expression of sialyl-dimeric LeX antigen in liver metastases of human colorectal carcinoma. Cancer Res, 49: 6883-6888, 1989.
5. Dohi, T., Nemoto, T., Ohta, S., Shitara, K., Hanai, N., Nudelman, E., Hakomori, S., and Oshima, M. Different binding properties of three monoclonal antibodies to sialyl Le(x) glycolipids in a gastric cancer cell line and normal stomach tissue. Anticancer Res, Vol. 13, pp. 1277-1282, 1993.
6. Koenig, A., Norgard-Sumnicht, K., Linhardt, R., and Varki, A. Differential interactions of heparin and heparan sulfate glycosaminoglycans with the selecting. Implications for the use of unfractionated and low molecular weight heparins as therapeutic agents. J Clin Invest, 101: 877-889, 1998.
7. Kawashima, H., Atarashi, K., Hirose, M., Hirose, J., Yamada, S., Sugahara, K., and Miyasaka, M. Oversulfated chondroitin/dermatan sulfates containing GlcAbeta1/IdoAalpha1-3GalNAc(4,6-O-disulfate) interact with L- and P-Selectin and chemokines. J Biol Chem, 277: 12921-12930, 2002.
8. Stevenson, J. L., Choi, S. H., and Varki, A. Differential metastasis inhibition by clinically relevant levels of heparins—correlation with selectin inhibition, not antithrombotic activity. Clin Cancer Res, 11: 7003-7011, 2005.
9. Monzavi-Karbassi, B., Artaud, C., Jousheghany, F., Hennings, L., Carcel-Trullols, J., Shaaf, S., Korourian, S., and Kieber-Emmons, T. Reduction of Spontaneous Metastases through Induction of Carbohydrate Cross-Reactive Apoptotic Antibodies. J Immunol, 174: 7057-7065, 2005.
10. Kawashima, H., Hirose, M., Hirose, J., Nagakubo, D., Plaas, A. H., and Miyasaka, M. Binding of a large chondroitin sulfate/dermatan sulfate proteoglycan, versican, to L-Selectin, P-Selectin, and CD44. J Biol Chem, 275: 35448-35456, 2000.
11. Cosgrove, R. H., Zacharski, L. R., Racine, E., and Andersen, J. C. Improved cancer mortality with low-molecular-weight heparin treatment: a review of the evidence. Semin Thromb Hemost, 28: 79-87, 2002.
12. Nelson, R. M., Cecconi, O., Roberts, W. G., Aruffo, A., Linhardt, R. J., and Bevilacqua, M. P. Heparin oligosaccharides bind L- and P-Selectin and inhibit acute inflammation. Blood, 82: 3253-3258, 1993.
13. Borsig, L., Wong, R., Hynes, R. O., Varki, N. M., and Varki, A. Synergistic effects of L- and P-Selectin in facilitating tumor metastasis can involve non-mucin ligands and implicate leukocytes as enhancers of metastasis. Proc Natl Acad Sci USA, 99: 2193-2198, 2002.
14. Wei, M., Tai, G., Gao, Y., Li, N., Huang, B., Zhou, Y., Hao, S., and Zeng, X. Modified heparin inhibits P-Selectin-mediated cell adhesion of human colon carcinoma cells to immobilized platelets under dynamic flow conditions. J Biol Chem, 279: 29202-29210, 2004.
15. Ma, Y. Q. and Geng, J. G. Heparan sulfate-like proteoglycans mediate adhesion of human malignant melanoma A375 cells to P-Selectin under flow. J Immunol, 165: 558-565, 2000.
16. Nazaruk R A, Rochford R, Hobbs M V, Cannon M J. Functional diversity of the CD8+ T cell response to Epstein-Barr virus: Implications for the pathogenesis of EBV-associated lymphoproliferative disorders. Blood 1998; 91:3875-83.
17. Miller, V. M. et al. 2004, Nucleic Acids Res. 32:661-668.
18. McManus, M T et al., 2002, Nature Rev. Genet. 3:737-747.
19. Miller, V M et al., 2003, Proc. Natl. Acad. Sci. USA 100:7195-7200.
20. U.S. Published Patent Application No. 20060154370.
21. Kitagawa, H et al. 2003, J. Biol. Chem. 278:23666-23671.
22. Sugahara, K et al., 2003, Current Opinion in Structural Biology 13:612-620.

All references cited in this specification are hereby incorporated by reference in their entirety. The discussion of the references herein is intended merely to summarize the assertions made by their authors and no admission is made that any reference constitutes prior art relevant to patentability. Applicant reserves the right to challenge the accuracy and pertinence of the cited references.

What is claimed is:

1. A method of identifying a candidate drug to treat cancer comprising:
   testing one or more compounds for inhibiting a chondroitin sulfate synthesis enzyme to identify a compound that inhibits a chondroitin sulfate synthesis enzyme;
   wherein a compound that inhibits a chondroitin sulfate synthesis enzyme is a candidate drug to treat cancer; and
   providing the candidate drug for testing for inhibiting metastasis in an animal model of cancer or in human cancer patients.

2. The method of claim 1 wherein the chondroitin sulfate synthesis enzyme is selected from the group consisting of: chondroitin synthase, chondroitin-glucuronate C5-epimerase, chondroitin 4-O-sulfotransferase-1 (C4ST1), chondroitin 4-O-sulfotransferase-2 (C4ST2), chondroitin 4-O-sulfotransferase-3 (C4ST3), chondroitin 6-O-sulfotransferase (C6ST), chondroitin 6-O-sulfotransferase-2 (C6ST2), chondroitin 4-sulfate 6-O-sulfotransferase (GalNAc4S-6ST) and galactosaminyl uronyl 2-0 sulfotransferase (CS/DS2ST).

3. The method of claim 1 wherein the chondroin sulfate synthesis enzyme is a chondroitin sulfate 4-sulfotransferase (C4ST).

4. The method of claim 2 wherein the chondroitin sulfate synthesis enzyme is chondroitin-glucuronate C5-epimerase or chondroitin 4-sulfate 6-O-sulfotransferase (GalNAc4S-6ST).

5. The method of claim 1 further comprising:
   testing the candidate drug for inhibiting metastasis in an animal model of cancer or in human cancer patients.

6. The method of claim 1 wherein the compound is a small molecule of molecular weight less than 3,000 daltons.

7. A method of identifying a candidate drug to treat cancer comprising:
   testing one or more compounds for inhibiting a chondroitin sulfate synthesis enzyme to identify a compound that inhibits a chondroitin sulfate synthesis enzyme;
   wherein a compound that inhibits a chondroitin sulfate synthesis enzyme is a candidate drug to treat cancer; and
   testing the candidate drug for inhibiting metastasis in an animal model of cancer or in human cancer patients.

8. A method of identifying a candidate drug to treat cancer comprising:
   obtaining a candidate drug that has been shown to inhibit a chondroitin sulfate synthesis enzyme; and
   testing the candidate drug for inhibiting metastasis in an animal model of cancer or in human cancer patients.

9. The method of claim 8 wherein the chondroitin sulfate synthesis enzyme is selected from the group consisting of: chondroitin synthase, chondroitin-glucuronate C5-epimerase, chondroitin 4-O-sulfotransferase-1 (C4ST1), chondroitin 4-O-sulfotransferase-2 (C4ST2), chondroitin 4-O-sulfotransferase-3 (C4ST3), chondroitin 6-O-sulfotransferase (C6ST), chondroitin 6-O-sulfotransferase-2 (C6ST2), chondroitin 4-sulfate 6-O-sulfotransferase (GalNAc4S-6ST) and galactosaminyl uronyl 2-0 sulfotransferase (CS/DS2ST).

10. The method of claim 8 wherein the chondroin sulfate synthesis enzyme is a chondroitin sulfate 4-sulfotransferase (C4ST).

11. The method of claim 9 wherein the chondroitin sulfate synthesis enzyme is chondroitin-glucuronate C5-epimerase or chondroitin 4-sulfate 6-O-sulfotransferase (GalNAc4S-6ST).

12. The method of claim 1 wherein the compound is a small molecule of molecular weight less than 3,000 daltons.

* * * * *